United States Patent
Lee et al.

(10) Patent No.: US 7,481,766 B2
(45) Date of Patent: Jan. 27, 2009

(54) MULTIPLE-BLADE RETRACTOR

(75) Inventors: Andrew Lee, Orland, PA (US); David Gerber, West Chester, PA (US)

(73) Assignee: Synthes (U.S.A.), West Chester, PA (US)

( * ) Notice: Subject to any disclaimer, the term of this patent is extended or adjusted under 35 U.S.C. 154(b) by 0 days.

(21) Appl. No.: 10/917,560

(22) Filed: Aug. 13, 2004

(65) Prior Publication Data
US 2005/0080320 A1    Apr. 14, 2005

Related U.S. Application Data

(60) Provisional application No. 60/494,803, filed on Aug. 14, 2003.

(51) Int. Cl.
*A61B 1/32* (2006.01)
(52) U.S. Cl. .................................... 600/214
(58) Field of Classification Search ............... 600/184, 600/185, 190–193, 196–197, 199, 201, 206, 600/208, 210–218, 221–228, 235
See application file for complete search history.

(56) References Cited

U.S. PATENT DOCUMENTS

| | | | |
|---|---|---|---|
| 2,191 A | 7/1841 | Pitney |
| 55,511 A | 6/1866 | Leutz |
| 147,867 A | 2/1874 | Schumacher |
| 350,721 A | 10/1886 | Cooper |
| 351,548 A | 10/1886 | Watson |
| 361,087 A | 4/1887 | Schenck |
| 390,561 A | 10/1888 | Brown |
| 424,140 A | 3/1890 | Shuford |
| 563,236 A | 6/1896 | Penhall |
| 579,625 A | 3/1897 | Willbrandt |
| 583,932 A | 6/1897 | Pederson |
| 605,547 A | 6/1898 | Holland |
| 659,409 A | 10/1900 | Mosher |
| 751,475 A | 2/1904 | Vilbiss |

(Continued)

FOREIGN PATENT DOCUMENTS
EP    0307528    3/1989

(Continued)

*Primary Examiner*—Anu Ramana
(74) *Attorney, Agent, or Firm*—Stroock & Stroock & Lavan LLP

(57) ABSTRACT

A retractor with multiple blades for use in surgery. The retractor may comprise first and second elongated portions which are pivotally connected to each other. A first blade may be connected to the first elongated portion and a second blade may be connected to the second elongated portion. The retractor may also comprise a sliding bar having a third blade. The sliding bar may be associated with the first and second elongated portions such that movement of the elongated portions relative to each other may result in movement of the sliding bar and, consequently, movement of the third blade relative to the first and second blades. In one embodiment, the retractor may comprise a tension limiting device so that the third blade may remain relatively stationary as the first and second blades are moved. The retractor may also comprise a fourth blade operatively connected to the first and second elongated portions. The fourth blade may be moved independently of the other blades or may move with the other blades. Also disclosed is a method of retracting tissue.

26 Claims, 17 Drawing Sheets

U.S. PATENT DOCUMENTS

| | | | |
|---|---|---|---|
| 761,821 A | 6/1904 | Clark et al. | |
| 815,907 A | 3/1906 | Davis | |
| 831,592 A | 9/1906 | Ballard | |
| 1,014,799 A | 1/1912 | Arthur | |
| 1,018,868 A | 2/1912 | Breneman | |
| 1,025,265 A | 5/1912 | Grindle | |
| 1,090,746 A | 3/1914 | Nourse | |
| 1,094,575 A | 4/1914 | Joutras | |
| 1,119,794 A | 12/1914 | Boucher | |
| 1,194,319 A | 8/1916 | Pretts | |
| 1,500,227 A | 7/1924 | Breneman | |
| 2,075,534 A | 3/1937 | McCormack | |
| 2,083,573 A | 6/1937 | Morgan | |
| 2,374,863 A | 5/1945 | Guttman | |
| 2,579,849 A | 12/1951 | Newman | |
| 2,807,259 A | 9/1957 | Guerriero | |
| 2,844,144 A | 7/1958 | Massey | |
| 3,030,947 A | 4/1962 | Engelbert | |
| 3,038,467 A | 6/1962 | Sovatkin | |
| 3,470,872 A | 10/1969 | Grieshaber | |
| 3,745,992 A | 7/1973 | Poirier | |
| 3,750,652 A | 8/1973 | Sherwin | |
| 3,759,263 A | 9/1973 | Taylor | |
| 3,769,980 A | 11/1973 | Karman | |
| 3,840,014 A | 10/1974 | Ling et al. | |
| 3,893,454 A | 7/1975 | Hagelin | |
| 4,034,746 A | 7/1977 | Williams | |
| 4,130,113 A | 12/1978 | Graham | |
| 4,312,337 A | 1/1982 | Donohue | |
| 4,627,421 A * | 12/1986 | Symbas et al. | 600/232 |
| 5,019,081 A | 5/1991 | Watanabe | |
| 5,052,373 A * | 10/1991 | Michelson | 600/217 |
| 5,125,396 A | 6/1992 | Ray | |
| 5,176,129 A | 1/1993 | Smith | |
| 5,363,841 A * | 11/1994 | Coker | 600/211 |
| 5,569,300 A | 10/1996 | Redmon | |
| 5,618,260 A | 4/1997 | Caspar et al. | |
| 5,681,265 A * | 10/1997 | Maeda et al. | 600/219 |
| 5,741,261 A | 4/1998 | Moskovitz et al. | |
| 5,785,648 A | 7/1998 | Min | |
| 5,868,668 A | 2/1999 | Weiss | |
| 5,885,210 A | 3/1999 | Cox | |
| 5,885,291 A | 3/1999 | Moskovitz et al. | |
| 5,885,292 A | 3/1999 | Moskovitz et al. | |
| 5,891,147 A | 4/1999 | Moskovitz et al. | |
| 5,899,854 A | 5/1999 | Slishman | |
| 5,931,777 A | 8/1999 | Sava | |
| 5,984,922 A | 11/1999 | McKay | |
| 5,993,385 A * | 11/1999 | Johnston et al. | 600/213 |
| 6,024,696 A | 2/2000 | Hoftman et al. | |
| 6,024,697 A | 2/2000 | Pisarik | |
| 6,027,504 A | 2/2000 | McGuire | |
| 6,042,540 A * | 3/2000 | Johnston et al. | 600/213 |
| 6,074,343 A | 6/2000 | Nathanson et al. | |
| 6,080,105 A | 6/2000 | Spears | |
| 6,096,046 A | 8/2000 | Weiss | |
| 6,102,852 A | 8/2000 | Liu | |
| 6,110,106 A | 8/2000 | MacKinnon et al. | |
| 6,152,874 A | 11/2000 | Looney et al. | |
| 6,193,651 B1 * | 2/2001 | DeFonzo | 600/201 |
| 6,196,969 B1 * | 3/2001 | Bester et al. | 600/224 |
| 6,217,602 B1 | 4/2001 | Redmon | |
| 6,261,296 B1 | 7/2001 | Aebi et al. | |
| 6,280,379 B1 | 8/2001 | Resnick | |
| D448,080 S | 9/2001 | Moscarelli et al. | |
| 6,302,842 B1 | 10/2001 | Auerbach et al. | |
| 6,309,349 B1 | 10/2001 | Bertolero et al. | |
| 6,354,995 B1 * | 3/2002 | Hoftman et al. | 600/219 |
| 6,425,901 B1 | 7/2002 | Zhu et al. | |
| 6,450,952 B1 | 9/2002 | Rioux et al. | |
| 6,468,276 B1 | 10/2002 | McKay | |
| 6,530,883 B2 * | 3/2003 | Bookwalter et al. | 600/231 |
| 6,537,212 B2 | 3/2003 | Sherts et al. | |
| 6,547,793 B1 | 4/2003 | McGuire | |
| 6,551,316 B1 * | 4/2003 | Rinner et al. | 606/57 |
| 6,602,188 B2 | 8/2003 | Bolser | |
| 6,663,562 B2 | 12/2003 | Chang | |
| 6,702,741 B2 | 3/2004 | Rioux et al. | |
| 6,733,444 B2 | 5/2004 | Phillips | |
| 2002/0133060 A1 | 9/2002 | Doyle | |
| 2003/0055320 A1 | 3/2003 | McBride et al. | |
| 2003/0149341 A1 | 8/2003 | Clifton | |
| 2003/0191371 A1 | 10/2003 | Smith et al. | |
| 2004/0002629 A1 | 1/2004 | Branch et al. | |
| 2004/0024291 A1 | 2/2004 | Zinkel | |

FOREIGN PATENT DOCUMENTS

| | | |
|---|---|---|
| EP | 0455282 | 11/1991 |
| EP | 0951868 | 10/1999 |
| EP | 1053717 | 11/2000 |
| GB | 2080113 | 2/1982 |
| GB | 2196535 | 5/1988 |
| JP | 04096742 | 3/1992 |
| JP | 6225662 | 8/1994 |
| WO | WO9421179 | 9/1994 |
| WO | WO02069811 | 9/2002 |
| WO | WO03017847 | 3/2003 |

* cited by examiner

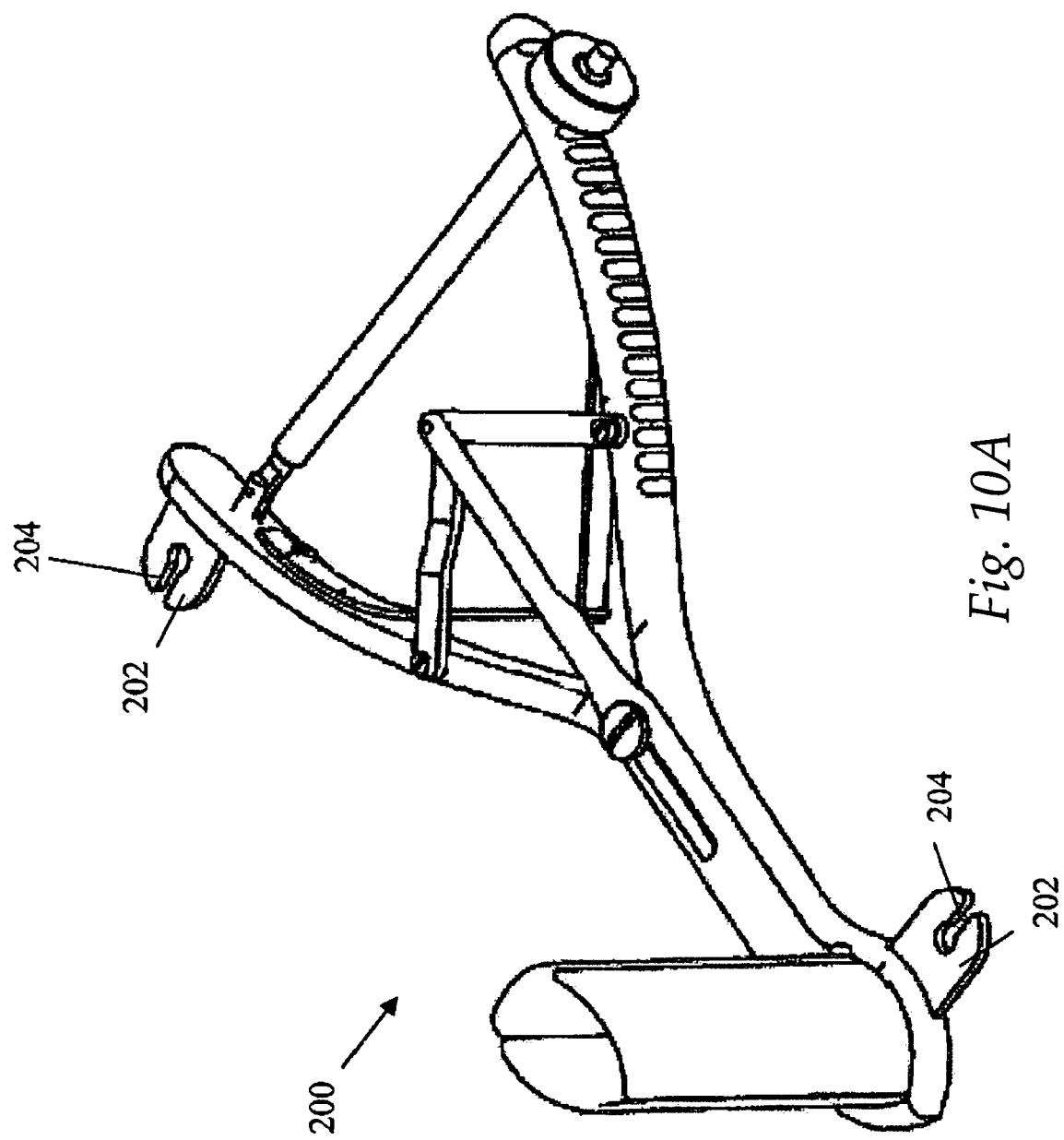

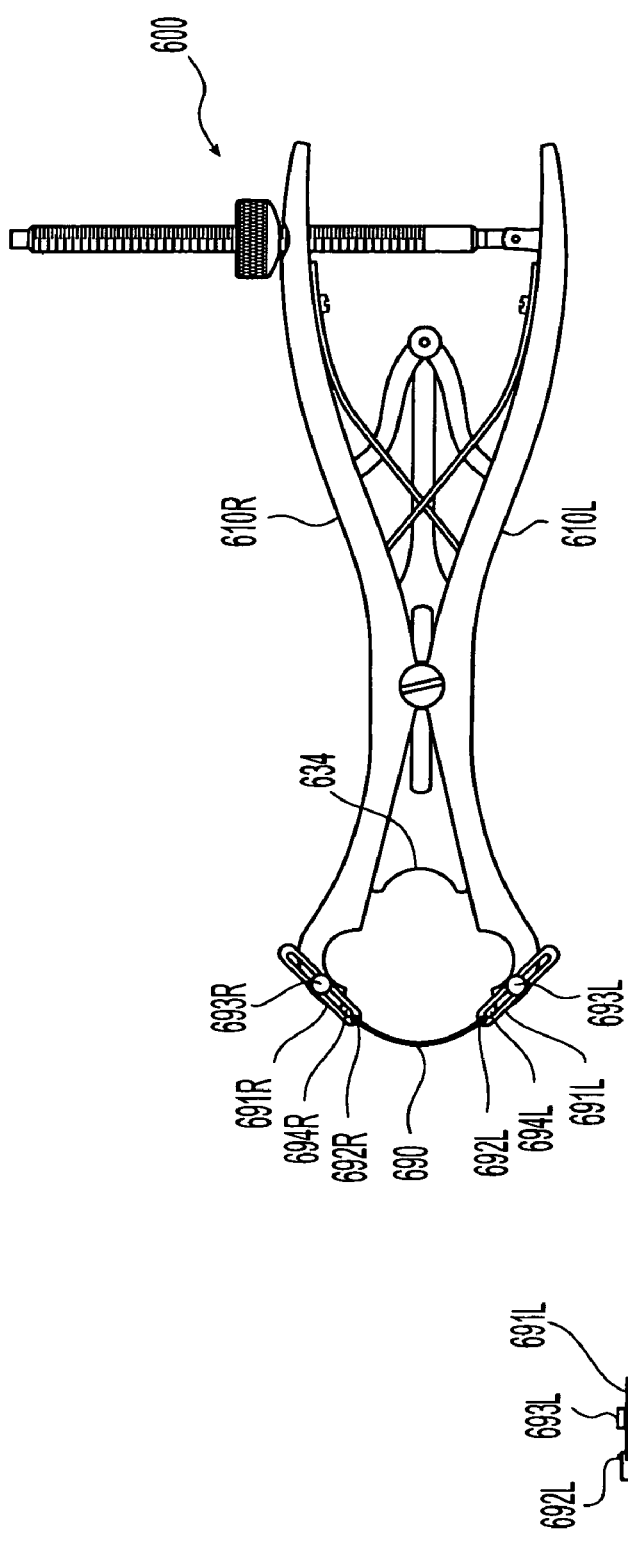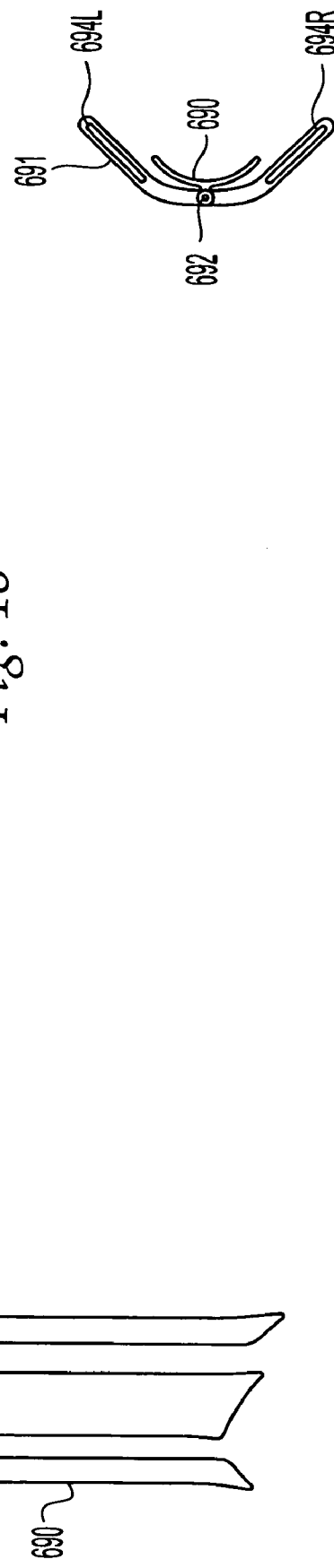
Fig. 18
Fig. 19
Fig. 20

MULTIPLE-BLADE RETRACTOR

CROSS REFERENCE TO RELATED APPLICATION

The present application claims priority to provisional application No. 60/494,803 filed on Aug. 14, 2003, the entire content of which is expressly incorporated herein by reference thereto.

FIELD OF THE INVENTION

The present invention relates generally to a multiple-blade retractor, and more particularly to a multiple-blade retractor for use in surgery to create minimally invasive access openings such as, for example, to the spine for discectomy, interbody fusion, and pedicle screw fixation.

BACKGROUND OF THE INVENTION

The subject disclosure relates to minimally invasive surgical procedures and apparatus and, more particularly, to an instrument for performing surgery associated with the spine. Retractors are used to secure an area opened during spinal surgery. A variety of retractors and blades have been used for this purpose. While these retractors and implements help keep the area open and the tissue retracted, they suffer from several disadvantages. For example, surgical instruments commonly used to secure the area opened during surgery are large and may require a large incision in order to be placed correctly and to allow the surgeon a sufficient field in which to work.

A need exists for an instrument that permits rapid surgical access to the desired area, permits a small incision, and is stable and safe during subsequent procedures.

SUMMARY OF THE INVENTION

The present invention generally relates to a multiple-blade retractor for use in surgery on the spine. A multiple-blade retractor may provide a larger opening than a traditional two-blade retractor which can only be opened in one direction, while still providing a smaller opening than the traditional open approach.

While the description of the retractor of the present invention relates to a multiple-blade retractor used in orthopedic surgery procedures, it should be understood that the retractor may also be used in other surgical procedures in which a surgeon wishes to gain access to an internal cavity by cutting the skin and entering a patient's body. The retractor may be used to maintain the incision in a spread apart condition so that surgical instruments may be inserted therethrough and surgical procedures may be performed on a patient using the surgical instruments.

The retractor may comprise elongate portions having handles suitable for grasping by a user to manipulate and operate the retractor. The elongated portions may be moveable with respect to each other and, in particular, may be pivotally connected so that the elongated portions may move reciprocally relative to each other. The retractor may further comprise at least one blade connected to each elongated portion so that each blade may move reciprocally relative to the other, a locking mechanism so the blades may be locked at a distance from each other, a biasing member for biasing the handles of the elongated portions away from each other, a sliding bar having a blade at one end and a pivot point at the other, and a link connected to each elongated portion for connecting the elongated portions to the pivot point of the sliding bar. Moreover, one or more blades may have flared tips to facilitate soft tissue engagement and reduce the risk of the blades slipping out of place. Further, the blades may be shaped to adapt to the bony anatomy of the spine.

The retractor may further comprise a mechanism for removably attaching the blades to the elongated portions and sliding bar, a fourth blade, blades of radiolucent material, an integrated light source or an attachment for a light source on one or more blades, a connecting portion for attaching the retractor, for example, to an operating table, an integrated suction/irrigation tool or an attachment for a suction/irrigation tool on one or more blades, blades of adjustable length, a supporting member for additional stability, a blade that may be permanently attached or detachable, and non-glare and/or scratch resistant finishes or coatings. In other embodiments, the location where the links attach to the arms may be varied to change the amount the sliding bar moves for a given movement of the elongated portions. In another embodiment, a spring may be attached to the sliding bar and may limit the movement of the sliding bar.

The multiple-blade retractor may be provided as an individual component, or it may be provided as part of a kit, which may include, for example, the multiple-blade retractor, and one or more two-bladed retractors or two-bladed hinged retractors. Further, the multiple-bladed retractor may be provided with a multiplicity of interchangeable blades comprising various lengths, materials, and surface configurations, as well as various springs for the force-limiting sliding blade embodiments. In addition, a kit may contain, for example, a light source, suction/irrigation tool, flat blades, blades of various lengths, and blades of various engagement angles.

BRIEF DESCRIPTION OF THE DRAWINGS

The present invention can be better understood by reference to the following drawings, wherein like references numerals represent like elements. The drawings are merely exemplary to illustrate certain features that may be used singularly or in combination with other features and the present invention should not be limited to the embodiments shown.

FIG. 2A is a partial cross-sectional view through a blade of the multiple-blade retractor of FIG. 2.

FIG. 10A is a perspective view of another embodiment of the multiple-blade retractor with connecting portions;

FIG. 18 is a top view of another embodiment of a multiple-blade retractor with a fourth blade;

FIG. 19 is a partial side view of the multiple-blade retractor of FIG. 18;

FIG. 20 is a top view of an alternative fourth blade attachment of the multiple-blade retractor of FIG. 18;

DETAILED DESCRIPTION

The retractor described in FIGS. 1-24 may be used to perform surgical procedures in the spinal area including, but not limited to, discectomy, implant insertion, pedicle screw placement, and spinal rod placement. While the description of the retractor will be discussed primarily in relation to spinal surgery, it should be understood that the retractor of this invention may be used in other types of surgical procedures. For instance, the retractor may be used where a surgeon wishes to gain access within the body by cutting the skin and may provide an access location for surgical procedures performed on a patient using surgical instruments. In particular, the retractor may hold back soft tissue or organs to allow visibility and/or access for surgical instruments to the location in the patient's body to be operated on by a surgeon and may maintain an incision in a spread apart position so that surgical instruments can be inserted into a patient.

Moreover, the components of any retractor embodiment discussed herein may be made, for example, of metal, plastic, rubber, or combination or composite materials (i.e., a material made of two or more materials). For example, the components may be made from stainless steel, titanium, aluminum, an alloy, carbon fiber composite, or a polymer (e.g., polyvinyl chloride (PVC), polyethylene, polyesters of various sorts, polycarbonate, teflon coated metal, polyetherether ketone (PEEK), ultra high molecular weight polyethylene (UHMWPE)). In addition, various methods may be used to make the components of the retractors discussed above, including casting, extrusion, injection molding, compression molding, forging, machining, or transfer molding. And, the components may be joined together, for example, by gluing, casting or forging as a single piece, welding or brazing, or mechanically joined by screwing, riveting, or other appropriate means.

Figure 1:
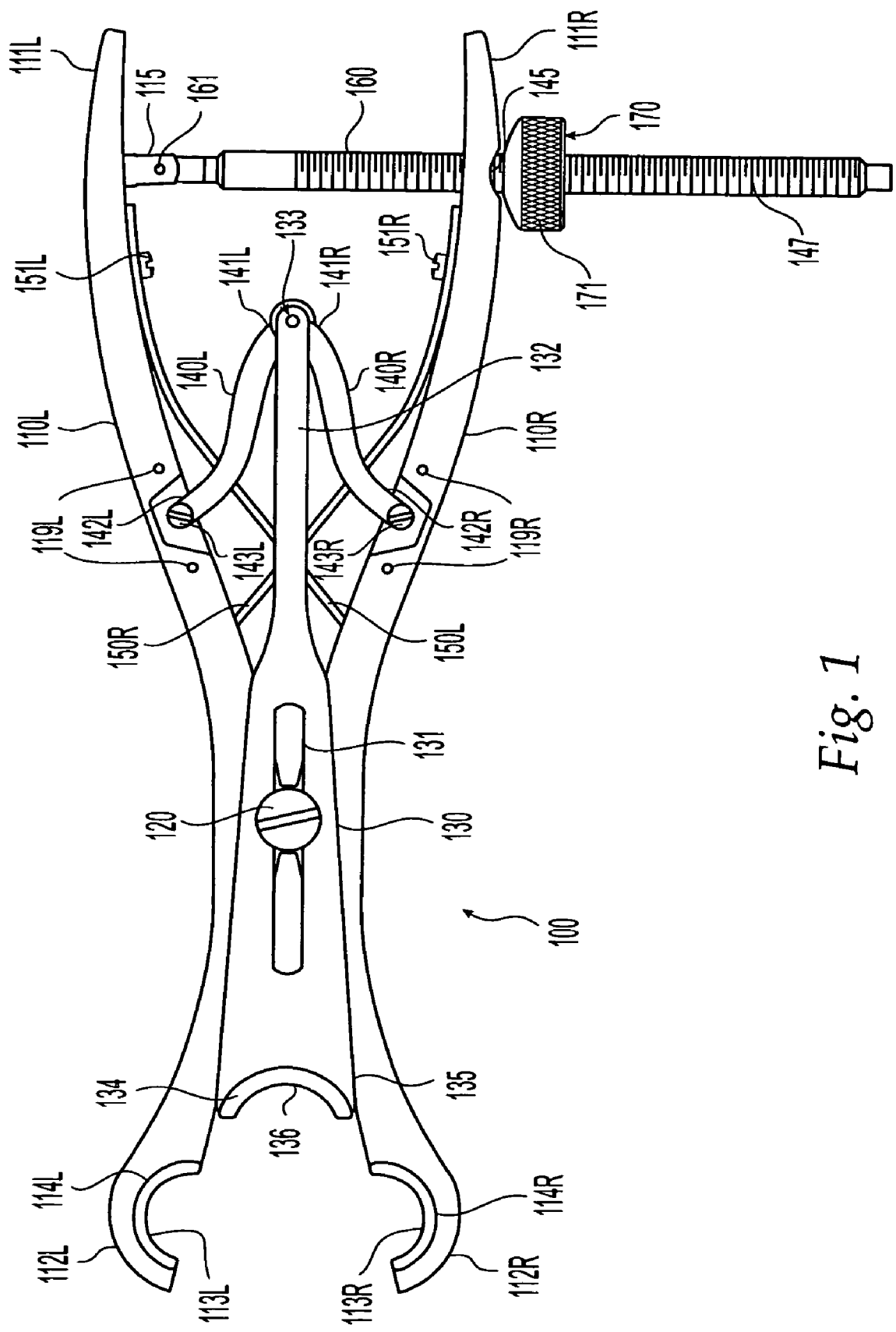
FIG. 1 is a bottom view of an embodiment of a multiple-blade retractor according to the present invention.

Referring now to FIG. 1, the multiple-blade retractor 100 may comprise at least two elongated portions 110R and 110L. It should, however, be understood that those of ordinary skill in the art will recognize many modifications and substitutions may be made to various elements of the retractor 100.

The elongated portions 110R, 110L may have a proximal end closest to an operator which may comprise handle portions 111R, 111L and a distal end opposite the proximal end which may comprise distal portions 112R, 112L. The handle portions 111R and 111L may be positioned at the proximal end of the elongated portions 110R and 110L, respectively, and may be designed to be grasped by a user. And the distal portions 112R and 112L may be positioned at the distal end of elongated portions 110R and 110L, respectively. Moreover, the elongated portions 110R and 110L may be pivotally connected, for example, by a pivot connector 120. The pivot connector 120 may be a bolt (with matching nut), pin, rivet, or other similar means of providing a pivot point. As such, the handle portions 111R, 111L and distal portions 112R, 112L may move reciprocally or opposite relative to each other. When the handle portions 111R, 111L are drawn together as shown in FIG. 1, the distal ends 112R, 112L (and thus opposing blades 113R and 113L) may be spread apart.

Figure 4:
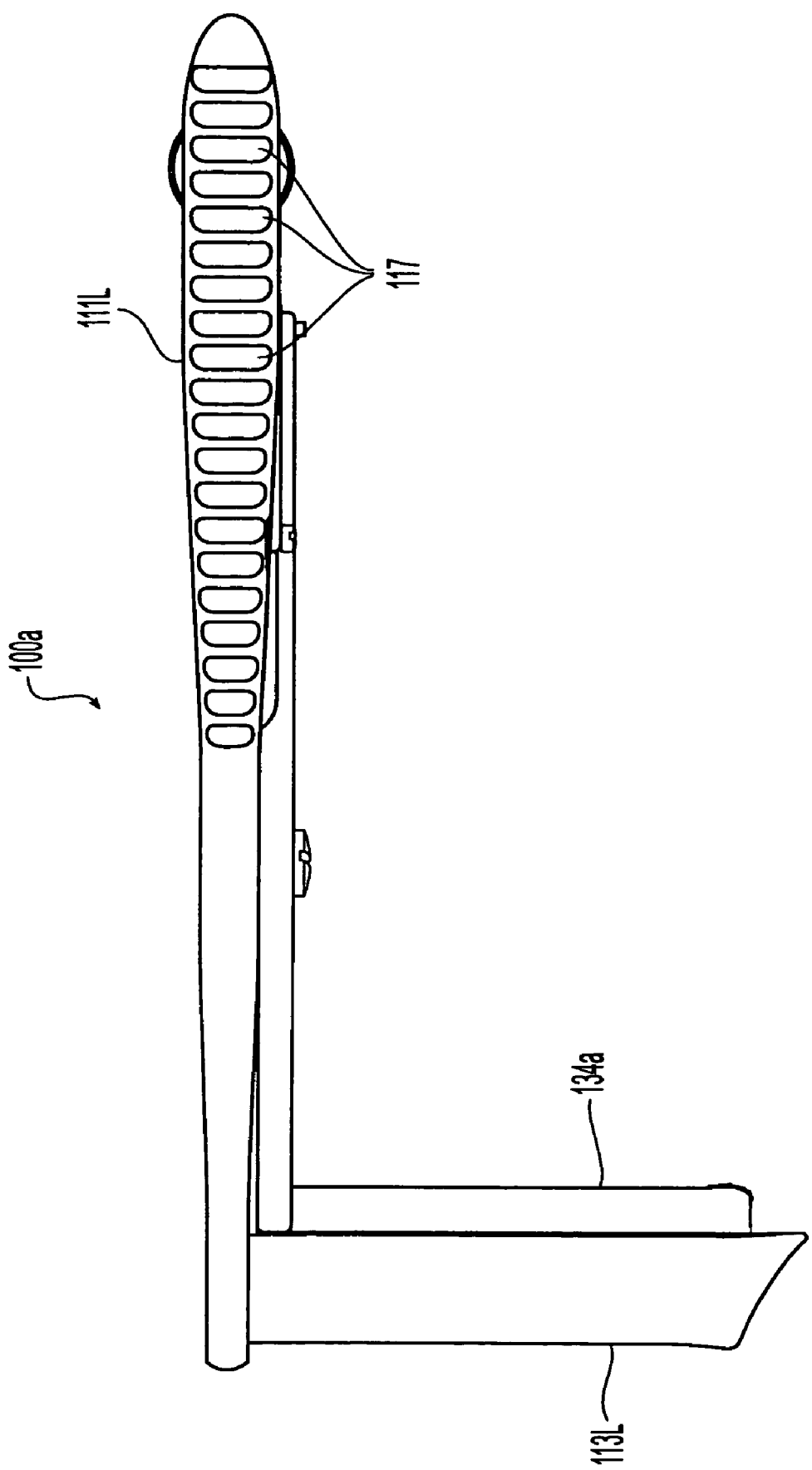
FIG. 4 is a side view of an alternative embodiment of a multi-blade retractor.
Figure 5:
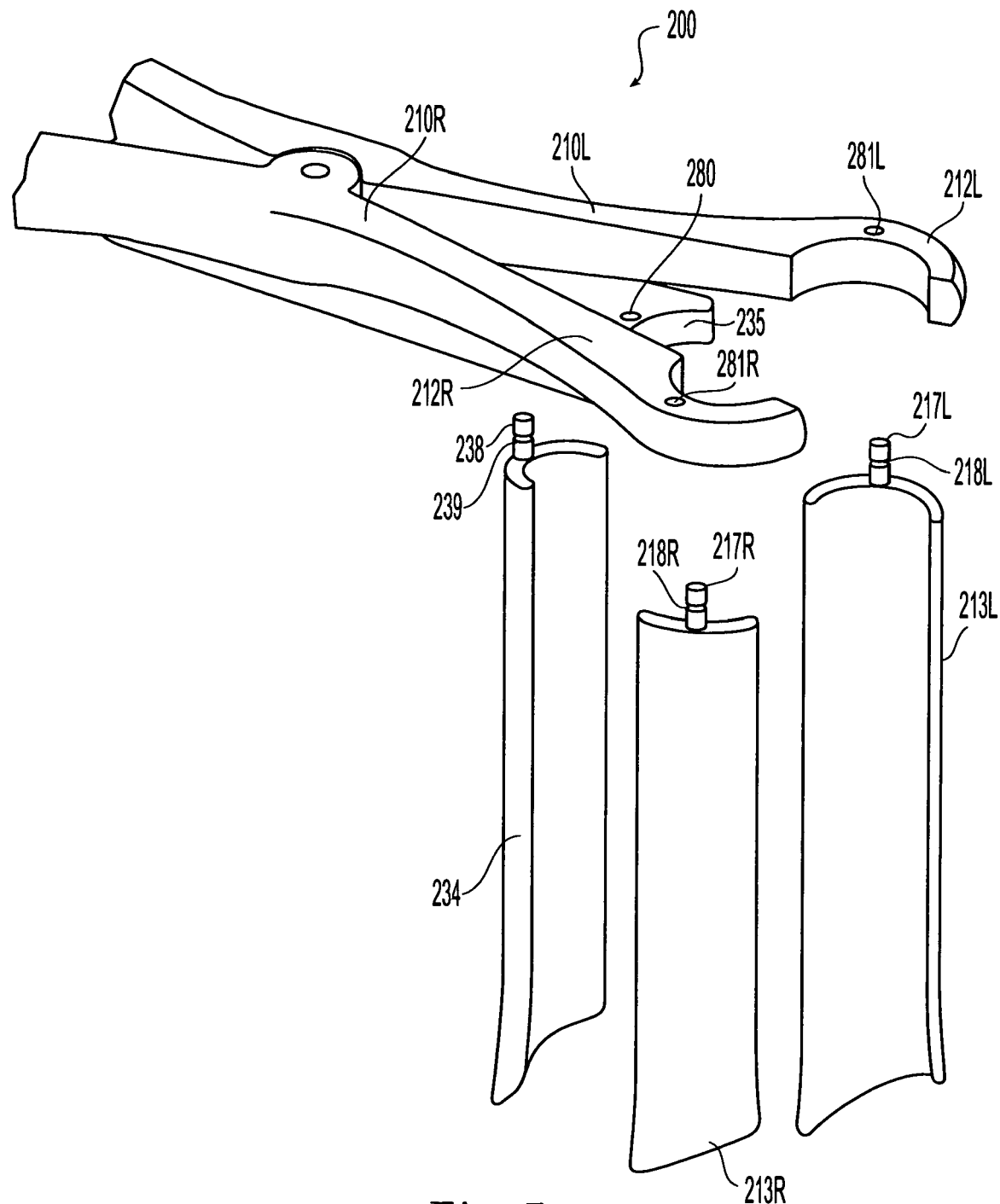
FIG. 5 is a partial perspective view of another embodiment of a multiple-blade retractor with detachable blades.

The handle portions 111R, 111L may have a grip 117 (FIG. 4) which may be integral with or connectable to the handle portions 111R and/or 111L and which may improve a user's grip of the retractor 100. The grip 117 may be made of the same or different material as the portions 110R, 110L. In one embodiment, the grip 117 may be a piece of material (e.g., plastic, rubber, etc.) positioned around the handle portions 111R, 111L. In another embodiment, the grip 117 may be bumps, protrusions or grooves formed on the handle portions 111R, 111L, which may be part of the structure of the handle portions 111R, 111L or may be separate pieces positioned on the handle portions 111R, 111L. For example, FIG. 4 shows multiple pieces of material positioned on the handle portion 111L.

Blades 113R and 113L may be attached to distal ends 112R and 112L, respectively, of elongated portions 110R, 110L. It should be understood that any reference to "blades" may not necessarily mean a cutting blade. While any blade described herein may have a cutting surface and/or may be used for cutting tissue, the retractor blades preferably function as walls that hold back soft tissue and prevent soft tissue from entering a surgical field. The blades 113R, 113L may be connected to the distal ends 112R, 112L, respectively, such that each blade 113R, 113L may move relative to the other blade 113R, 113L. In a closed position, the distal ends 112R, 112L may be in contact with each other and the blades 113R, 113L mounted on the distal ends 112R, 112L may define an initial retractor opening as shown in FIG. 10A. Depending on the shape and geometry of the blades 113R, 113L, the opening may be a circular space; however, the opening may be any shape. As shown in FIG. 1, blades 113R, 113L may have a concave-convex face profile, but blades having other configurations may also be used. Various factors may be considered when determining the design (e.g., size, shape, orientation) of the blades, including minimizing the trauma to the patient's body at the incision when the blades are spread apart, stabilizing the blades in the incision so they may not easily slip out of engagement with the retracted tissue, and allowing customization for each patient's anatomy.

A sliding bar 130 may be connected to the elongated portions 110R, 110L by pivot pin 120, which may be disposed through slot 131 of sliding bar 130. A sliding blade 134, in turn, may be mounted on distal end 135 of sliding bar 130 such that inner face 136 of sliding blade 134 may be adjacent to outside faces 114R and 114L of the blades 113R and 113L, respectively. As with blades 113R and 113L, the sliding blade 134 may have a concave-convex profile. Sliding blades 134 may have other configurations as well.

The proximal end 132 of sliding bar 130 may be pivotally connected to medial ends 141R, 141L of links 140R, 140L by pin 133. Alternative connection components may be used in place of pin 133 (e.g., a screw, bolt) so long as the connection component allows for rotation of links 140R, 140L thereabout. Lateral ends 142R, 142L of links 140R, 140L may be pivotally attached to elongated portions 110R, 110L by screws 143R, 143L. It should be understood that other connection components may be used in place of the screws 143R, 143L (e.g., a pin, bolt) so long as the connection component allows for rotation of links 140R, 140L thereabout. Holes 119R, 119L may also be provided in the elongated portions 110R, 110L to allow repositioning of the links 140R, 140L so that the movement of the sliding blade 134 may be adjusted with respect to the opposing blades 113R, 113L, as will be described in greater detail below. The holes 119R, 119L may be threaded or smooth. The sliding blade 134 may be connected along any portion of the elongated portions 110R and 110L by any direct or indirect method, including an intermediate linkage.

The links 140R, 140L may connect the sliding bar 130 and, consequently, the sliding blade 134 to the elongated portions 110R, 110L such that moving the handle portions 111R, 111L together may result in the sliding blade 134 moving away from the blades 113R, 113L by an amount proportional to the movement of the elongated portions 110R, 110L. If an operator connects the links 140R, 140L to different holes 119R, 119L, the amount the sliding blade 134 may move away from the blades 113R, 113L relative to the movement of the elongated portions 110R, 110L may change. For example, connecting the links 140R, 140L at a position on the elongated portions 110R, 110L closer to the pin 120 may result in the sliding blade 134 moving a smaller distance away from the blades 113R, 113L than if the links 140R, 140L were connected at a position on the elongated portions 110R, 110L farther from the pin 120. Changing the position of the links 140R, 140L may also affect the location of the sliding blade 134 relative to the blades 113R, 113L when the retractor 100 is in a closed position.

Moreover, leaf springs 150R, 150L may be positioned between the elongated portions 110R, 110L and may be connected to elongated portions 110R, 110L by screws 151R, 151L. It should be appreciated by those skilled in that art that this connection may alternatively be made using rivets, welding or other fastening mechanisms. The leaf springs 150R, 150L may bias the handle portions 111R, 111L in a spread apart position such that the retractor blades 113R, 113L and sliding blade 134 may be in the closed position. In another embodiment, a coil spring (not shown) may be used to bias the handle portions 111I R, 111L in a spread apart position. However, other components and different components and mechanisms may be used to bias the handle portions 111R, 111L apart.

In use, as handle portions 111R, 111L are brought together, the links 140R, 140L may rotate about screws 143R, 143L such that medial ends 141R, 141L may move in the proximal direction (i.e., away from the blades 113R, 113L). As the medial ends 141R, 141L move proximally, they pivot about pin 133 and pull the sliding bar 130 proximally. The linear movement of the sliding bar 130 is guided by pivot pin 120 interacting with and moving in slot 131. As sliding bar 130 moves proximally, sliding blade 134 may move in the proximal direction. Upon releasing pressure from the handle portions 111R, 111L, the leaf springs 150R, 150L may cause the handle portions 111R, 111L to spread apart. As a result, the elongated portions 110R, 110L and sliding blade 130 may return to the closed position where the blades 113R and 113L may be in close proximity and the inside face 136 of sliding blade 134 may be adjacent to the outside faces 114R, 114L of the blades 113R, 113L.

A locking mechanism may also be provided to lock the blades 113R, 113L and 134 at a selected distance from each other. As shown in FIG. 1, the locking mechanism may comprise a threaded bar 160 pivotally connected by a pin 161 to a flange 115 on the inner side of handle portion 111L. The opposite end of threaded bar 160 may be slidably received within a bore 145 in handle portion 111R, such that a portion 147 of the threaded bar 160 extends past handle portion 111R. A nut 170 may be threaded onto the portion 147 of threaded rod 160 and may be tightened against the handle portion 110R, thereby preventing spreading of the handle portions 110R, 110L. The nut 170 may have an outer knurled surface 171, which may enhance a user's grip on the nut 170 during tightening and loosening of the nut 170. Alternatively, the locking mechanism may be configured in the opposite arrangement so that the threaded bar 160 passes through the handle portion 110L and the nut 170 engages the handle portion 110L. One skilled in the art would recognize that the locking mechanism can be a ratchet, a "soft lock" arrangement, or any other appropriate locking mechanism known in the art.

In the closed position, blades 113R, 113L, and 134 may generally form a circular opening with an inside diameter between about 3 mm and about 50 mm, more preferably, between about 10 mm and 16 mm and, most preferably, about 13 mm. It should be understood by those of skill in the art that the blades 113R, 113L, and 134 may be of any size suitable to be inserted into a surgical incision in a patient undergoing a surgical procedure, and thereafter be spread apart to form an opening through which medical instruments may be inserted to perform exploratory, diagnostic, or surgical procedures.

In the opened position, the blades 113R, 113L, and 134 may form an access opening—for example, a roughly triangular (e.g., isosceles triangle) or four pointed opening—having a dimension, for example, of between about 10 mm and about 150 mm by between about 10 mm and about 50 mm, and more preferably about 70 mm by about 30 mm. The opening may be other shapes and sizes depending on blade geometry and size. Furthermore, in the open position, the distance between the blades 113R and 113L may be, for example, between about 10 mm and about 150 mm. The distance between the sliding blade 134 and the blades 113R, 113L, for example, may be between about 0 mm and about 50 mm.

Figure 2:
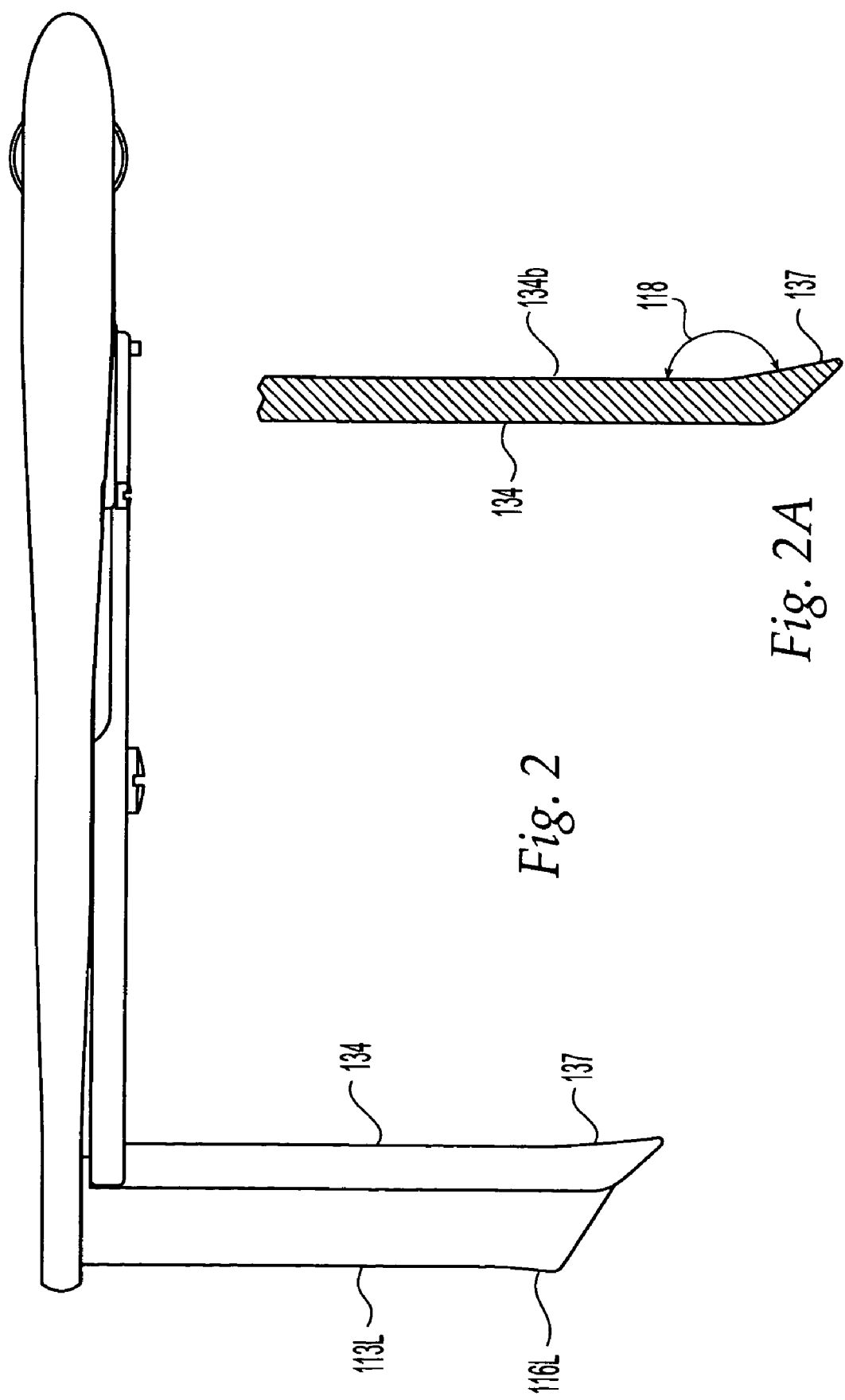
FIG. 2 is a side view of the multiple-blade retractor of FIG. 1 in a closed position.
Figure 3:
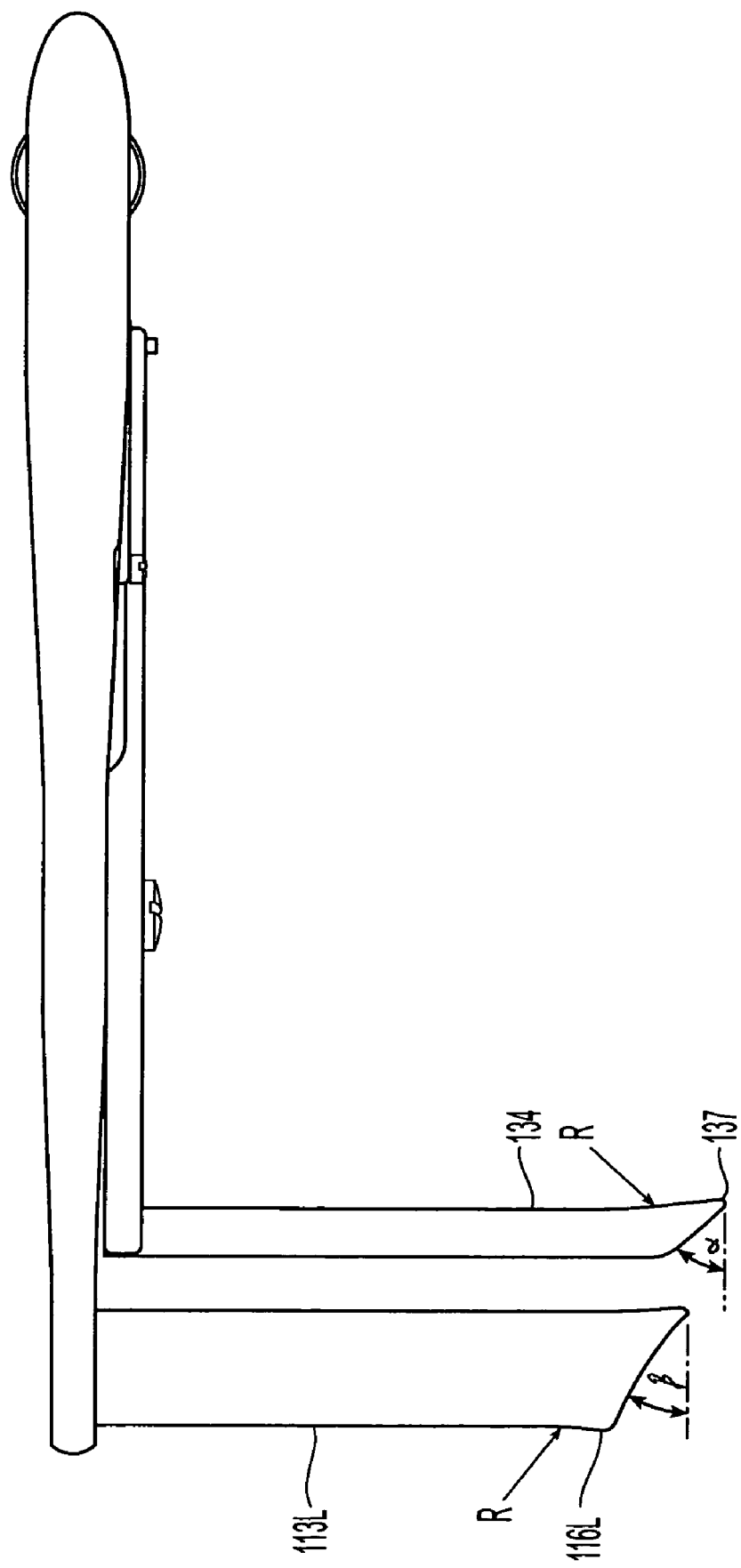
FIG. 3 is a side view of the multiple-blade retractor of FIG. 1 in an open position.

As shown in FIGS. 2 and 3, the blades 113L and 134 may have outwardly flared tips 116L and 137 with radii R to facilitate soft tissue engagement. The blade 113R may also have a flared tip (not shown) with a radius R. It should be understood that a flared tip may be any type of curve or angle. In one embodiment, the flared tips may be at an angle with the wall of the blades. For example, with reference to blade 134 in FIG. 2A, the flared tip 137 may be at an angle 118 with a wall 134b of the blade 134. The angle 118 may, for example, be between about 90 and about 180° and, more preferably, between about 135 and about 180°. One or more blades may have a flared tip or no blade may have a flared tip. In another embodiment, some blades may have a radius R, while other blades may have an angle 118. In yet another embodiment, all blades may have radii R or all blades may have an angle 118. And, the radius R and/or angle 118 of each blade may be the same as or different from the radius R and/or angle 118 of the other blades. It should also be understood that any blade may be flared or angled along its entire length. A flared tip may facilitate soft tissue engagement (i.e., enhance the grip on the underside of a patient's tissue) and, thus, may prevent inadvertent or premature dislodging or slipping of the retractor 100 from an incision. A flared tip such as tips 116L and 137 may also be used to adapt the retractor 100 to the bony anatomy of the spine.

Moreover, the blades 113R, 113L and 134 may take on various shapes and sizes depending on the surgical procedure in which the retractor is to be used. The tips of the blades 113R, 113L and 134 may be adapted to conform to the bony anatomy of the spine. For example, the blades 113R, 113L and 134 may be configured to contact a portion of a spinal lamina.

To achieve this conformity, the angle α of tip 137 of the sliding blade 134 may be between about 0 and about 70° and, more preferably, between about 20 and about 40°. The angle β of the tip 116L of the blade 113L and the tip (not shown) of the blade 113R may be between about 0° and about 80° and, more preferably, about 30° and about 60°. The lengths of the blades 113R, 113L (including the angled tips) may be between about 25 mm and about 200 mm and, more preferably, between about 80 mm and about 110 mm. Radii R at the flaring ends of blades 113R, 113L and/or 134 (where concave-convex blades are provided) may be between about 0 mm and about 100 mm and, more preferably, between about 0 mm and about 50 mm. The blades 113R, 113L and/or 134 may be curved from their distal tips and the curve may extend for a length of between about 0 mm and about 30 mm of the blades 113R, 113L and/or 134 and, more preferably, for about the distal 0 mm to about 20 mm of the blades 113R, 113L and/or 134. And, the blades 113R, 113L, and blade 134 may be approximately the same length or they may be of different combinations of lengths, as is appropriate for a particular procedure and patient.

For example, as shown in FIGS. 2 and 3, the sliding blade 134 may be longer than the blades 113R, 113L. In such a configuration, the retractor 100 may function as a lateral retractor. As a lateral retractor, for example, when a patient is laying on his/her stomach, the retractor 100 may be positioned so that the handle portions 111R, 111L of the retractor 100 may be at an angle (e.g., approximately perpendicular) with the spine of a patient or otherwise pointing towards the side of a patient. In this orientation, the blades 113R, 113L may be positioned over the spine and, because of their shorter length, may avoid contact with spinal bones. The longer sliding blade 134 may be positioned along the side of the spine and may penetrate deeper into the back of a patient.

As shown in FIG. 4, in another embodiment, the sliding blade 134a may be shorter than the blades 113L, 113R. In such a configuration, the retractor 100a may function as a medial retractor. As a medial retractor, for example, when a patient is laying on his/her stomach, the retractor 100a may be positioned so the handle portions 111R, 111L of the retractor 100a may be parallel to the spine of a patient. In this orientation, the sliding blade 134 may be positioned over the spine and, because of its shorter length, may avoid contact with spinal bones. On the other hand, the longer blades 113R, 113L may be positioned along the side of the spine and may penetrate deeper into the back of a patient.

Moreover, the blades 113R, 113L and/or 134 of the retractor 100 of FIGS. 1-3 may be permanently attached to the elongated portions 110R, 110L or sliding bar 132, respectively, by, for example, welding, brazing, soldering or may be formed integrally with the elongated portions 110R, 110L or sliding bar 132. In an alternate embodiment, shown in FIG. 5, blades 213R, 213L and/or 234 of the retractor 200 may be detachable. Detachable blades may allow a surgeon to install blades of various lengths, shapes, and/or materials to account various factors, including the differences in patient anatomy, part of the body where surgery may be performed, and whether radiolucence may be desireable.

The blades 213R, 213L, and 234 may have protrusions 217R, 217L, and 238, respectively. Grooves 218R, 218L, and 239 may be provided in protrusions 217R, 217L, and 238 to mate with ball detents (not shown), which may be positioned within the holes 281R, 281L, and 280. The ball detents may comprise, for example, ball bearings (not shown) operatively connected to a biasing means (e.g., a spring) such that the ball bearings may move in and out of holes 281R, 281L and 281 to engage/disengage the grooves 218R, 218L, and 239. The holes 281R, 281L, and 281 may be located in distal portions 212R, 212L of elongated portions 210R, 210L and in the sliding bar 235. In alternative embodiments, other means of removably attaching the blades 213R, 213L and/or 234 may be used, such as threaded connections, set screws, pins, etc. The blades 213R, 213L and/or 234 may freely rotate with respect to the elongated portions 210R, 210L and/or the sliding bar 235 or may have keyed connections with the elongated portions 210R, 210L and/or the sliding bar 235 to maintain a fixed relative orientation between the blades 213R, 213L and/or 234 and the elongated portions 210R, 210L and/or the sliding bar 235.

Figure 6:
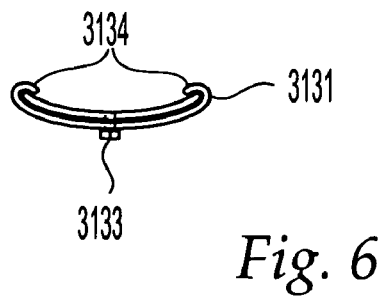
FIG. 6 is an end view of a telescoping retractor blade.
Figure 7:
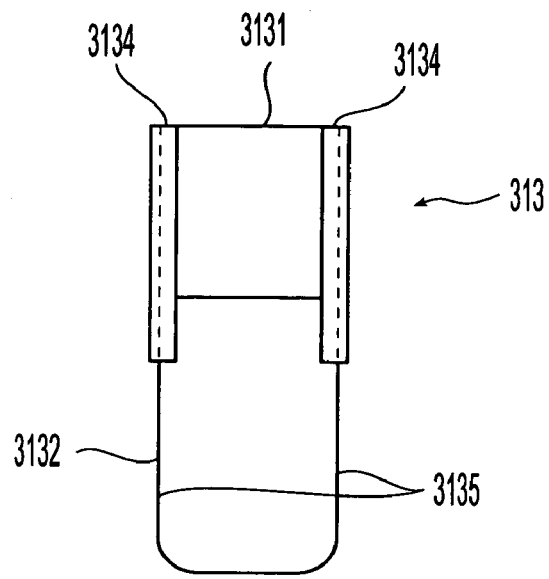
FIG. 7 is a side view of the inside face of the telescoping retractor blade of FIG. 6.
Figure 8:
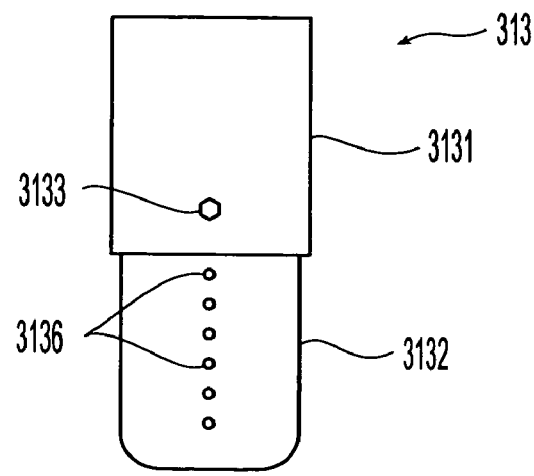
FIG. 8 is a side view of the outside face of the telescoping retractor blade of FIG. 7.

As shown in FIGS. 6-8, in another embodiment of the present invention, the retractor 100 may comprise a variable length telescoping retractor blade 313. Variable length blades may allow a surgeon to select the length of each blade to account for differences in patient anatomy or the type of surgery to be performed while minimizing the inventory of blades that would be required if detachable blades were used. The telescoping retractor blade 313 may comprise an upper blade portion 3131 and a lower blade portion 3132. The lower blade portion 3132 may be positioned within upper blade portion 3131 and may slide axially therein. The upper blade portion 3131 may comprise lips 3134, which may encircle outer edges 3135 of the lower blade portion 3132. Such a construction may prevent all motion of the lower blade portion 3132 in relation to the upper blade portion 3131 except in an axial direction. The engaging portion 3133 may extend through a hole (not shown) in upper blade portion 3131 and may be selectively engaged in one of a series of linearly disposed depressions 3136 in lower blade portion 3132. In one embodiment, holes through the lower blade portion 3132 may be used in place of or in addition to the depressions 3136. Thus, the lower blade portion 3132 may be fixed in relation to the upper blade portion 3131. In one embodiment of the present invention, the engaging portion 3133 may be a screw positioned within a threaded hole (not shown) in the upper blade portion 3131.

The lower blade portion 3132 may be slid axially (i.e., up or down) within the upper blade portion 3131 to adjust the length of the telescoping blade 313. Thereafter, the position of the two blades may be locked by positioning the engaging portion 3133 in the appropriate depression 3136. It will be understood that any other means of locking the lower blade portion 3132 to the upper blade portion 3131 may be used so long as the position of the blades relative to one another may be adjustable. For example, locking the lower blade portion 3132 to the upper blade portion 3131 may include the use of a ratchet means, a friction fit, or a leaf spring or ball detent in one blade portion engaging one of a selectable variety of depressions in the other blade portion.

In general, various factors may be considered when determining the material used to make any of the retractor blades discussed above, including the ability to withstand sterilization/cleaning (i.e., cleaning products used in sterilization in a hospital), weight, durability, mechanical strength (e.g., the ability to withstand stress from opening the retractor in a patient's body and maintaining the retractor in an open position), resistance to bacterial formation, ease and cost of manufacturing, biocompatibility and ability to withstand staining (i.e., from blood or other chemical products used in a hospital). Moreover, using a non-metallic blades (or, for that matter, any other component) may provide the benefit of the blade being radiolucent (i.e., transparent to x-rays or other form of radiation), which may allow better visualization of the surgical site using current imaging techniques. In addition, the blades or any other component of the retractor may include a non-glare surface finish, which may prevent light reflection and improve visualization in the surgical working space, and/or a scratch resistant coating, which may preserve the surface finish/coating.

Further, the outside faces of the retractor blades may be partially or fully padded or comprise a compressible material to minimize trauma to the surrounding tissue as the retractor is spread open. Thus, the retractor blades may be constructed of multiple layers—an inner layer which may be constructed of a stronger, stiffer material and an outer layer which may be spongy or padded. In one embodiment of the present invention, one layer may be sprayed onto another layer. The layers may be connected together, for example, by a bonding medium (e.g., adhesive), screws, pegs, bolts, or welding.

Figure 9:
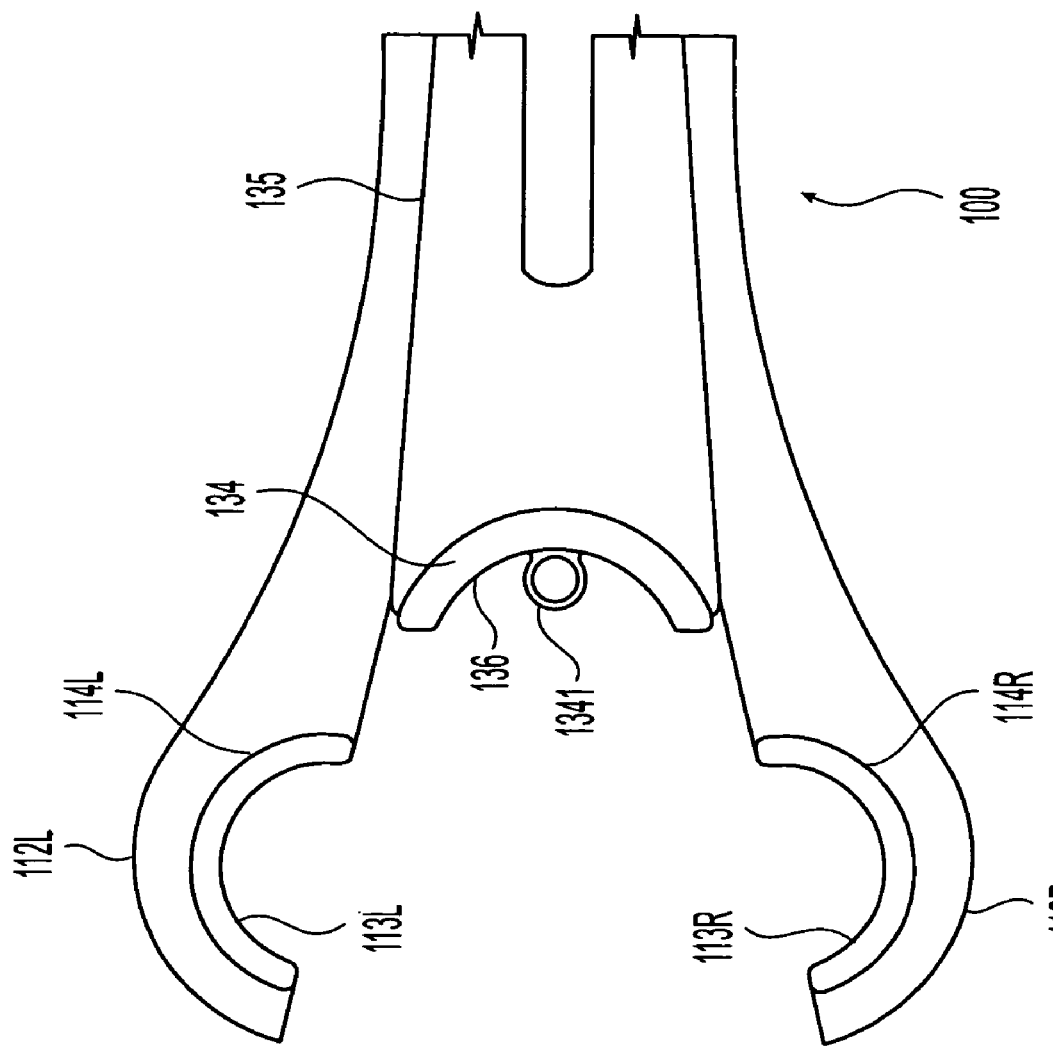
FIG. 9 is a partial bottom view of a blade of the multiple-blade retractor of FIG. 1 with a cannula for attaching a tool.

Turning now to FIG. 9, one or more of the blades 113R, 113L or 134 of retractor 100 may have a cannula 1341, which may be used to attach a device for use during surgery, for example, a light source, suction/irrigation tool, or viewing device. The cannula 1341 may extend only a short length along the blades 113R, 113L and/or 134 or may extend the entire length of the blades 113R, 113L and/or 134. Moreover, the cannula 1341 may be located at any position along the length of the blades 113R, 113L and/or 134 and may be any diameter appropriate for attaching tools, such as a light source, suction/irrigation instrumentation, or any other instrumentation required by the specific surgical procedures. Although not shown, the light source may comprise a fiberoptic bundle, and this bundle may be inserted within one of the cannulae 1341. Alternatively, the light source may be integrated into the blades 113R, 113L and/or 134, either being formed together with the blades or glued or otherwise bonded to the blades.

Figure 10:
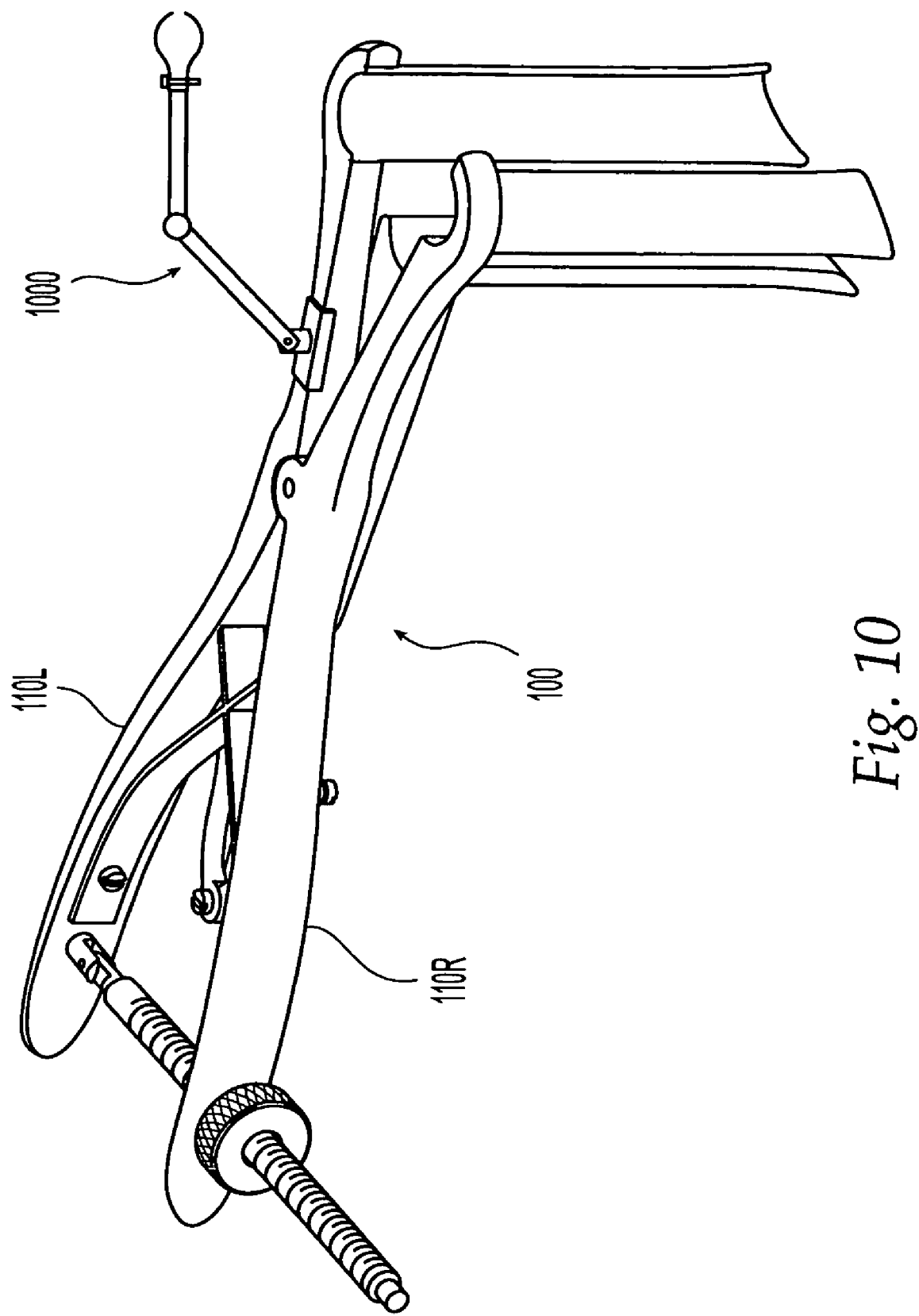
FIG. 10 is a perspective view of an embodiment of the multiple-blade retractor of FIG. 1 with an attachment for a tool.

Other means of attaching a surgical instrument are also envisioned. For example, as shown in FIG. 10, a movable arm 1000 may be attached to elongated portions 110R and/or 110L. A surgical instrument, for instance, a microscope or other similar viewing device may be removeably or permanently connected to the moveable arm 1000. The moveable arm 1000 may be bolted or clamped onto elongated portions 110R and/or 110L and may be releasably attached and/or moveable along elongated portions 110R and/or 110L. The moveable arm 1000 may alternatively be permanently attached to elongated portions 110R and/or 110L. The moveable arm 1000 may be a ball and socket type articulating arm, flexible arm, or other device allowing an instrument to be attached and moved relative to three-blade retractor 100.

In the embodiment of FIG. 10A, a retractor 200 may comprise one or more connection portions 202, which may be used to engage a support structure (not shown). The support structure, which may be rigid or flexible (e.g., flex arm), and may, in turn, be connected, for example, to an operating table to hold the retractor 200 in place relative to a patient during surgery. The connection portion 202 may be any shape or size and may have an opening 204 to receive another component (not shown). Alternatively, the connection portion 202 may have no opening 204. Moreover, the connection portion 202 may have a clip or hook (not shown) to engage a clip or hook engaging portion of another component (not shown). The connection portion 202 may be integral with or a separate piece connectable to the retractor 200. It should, however, be understood that any construction of the connection portion 202 is envisioned so long as the connection portion 202 may be used to connect the retractor 200 to another component.

Figure 11:
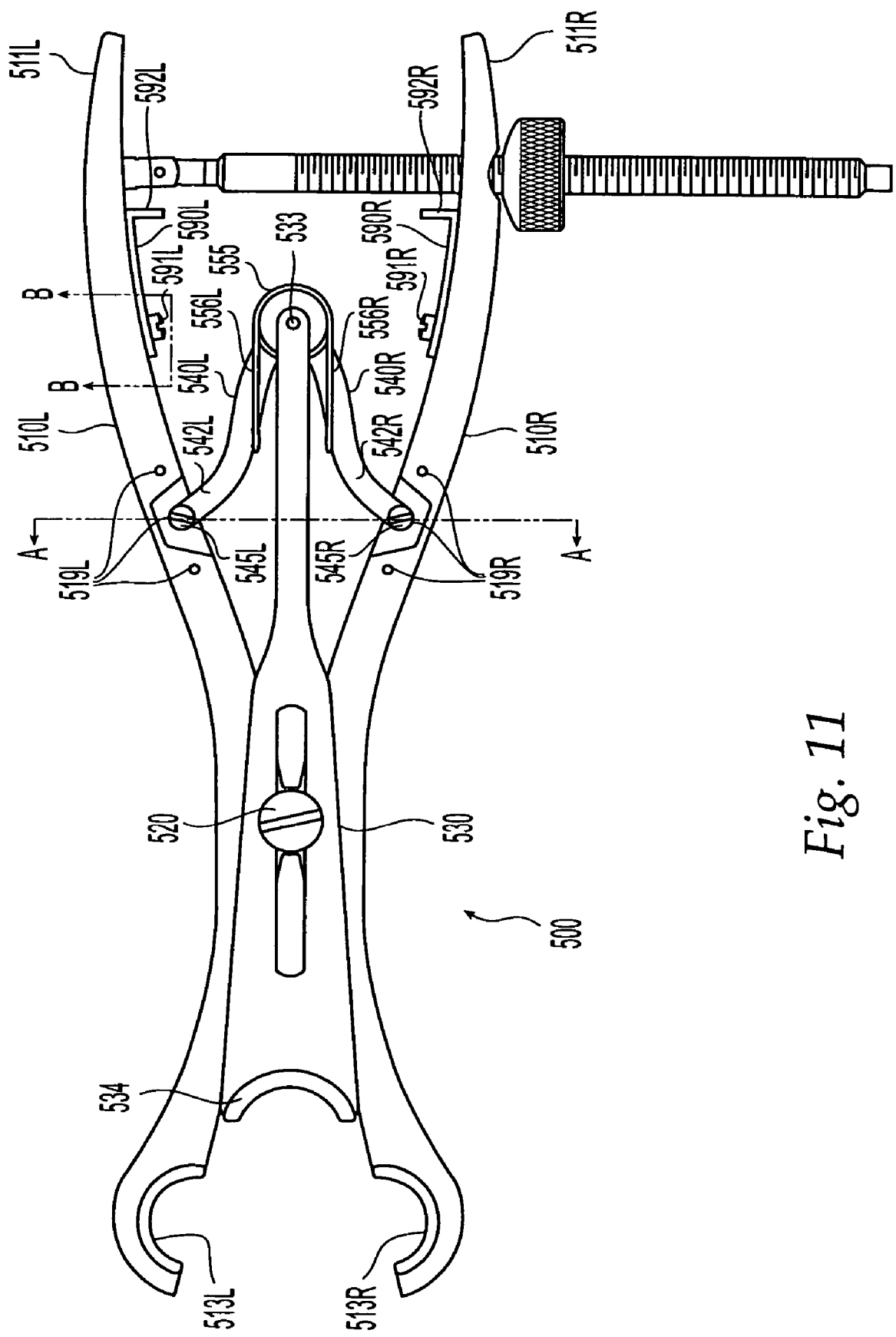
FIG. 11 is a bottom view of another embodiment of a multiple-blade retractor with a biasing member and support members.
Figure 12:
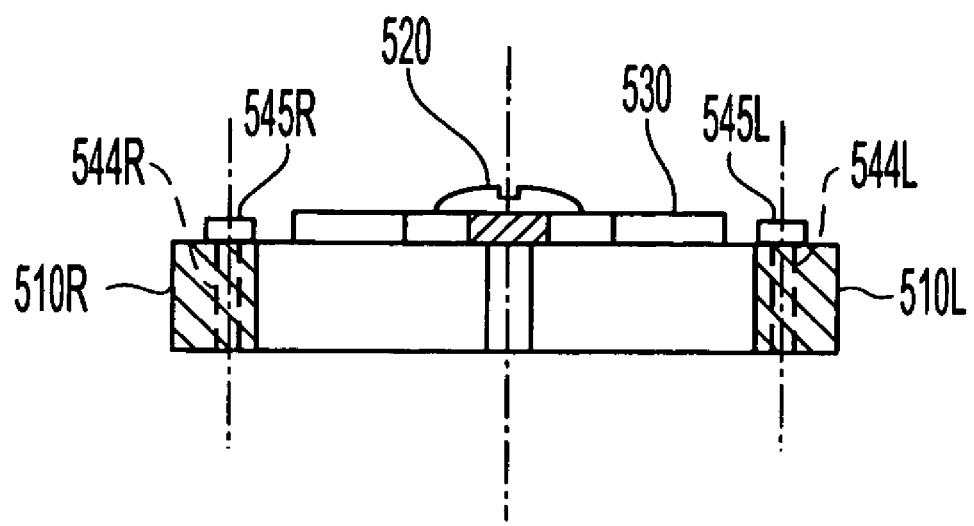
FIG. 12 is a cross-sectional view of the multiple-blade retractor of FIG. 11 along A-A.
Figure 13:
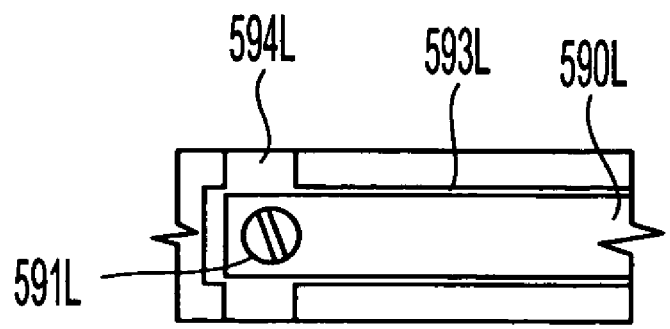
FIG. 13 is a detail view of a support member of the multiple-blade retractor of FIG. 11 along B-B.

Another embodiment of the retractor is shown in FIGS. 11-13. The retractor 500 may operate similar to the retractor 100 of FIGS. 1-3. And, similar to the retractor 100, the construction of the retractor 500 may permit the stroke of a sliding blade 534 to be varied in relation to the movement of the blades 513R and 513L. This may provide the advantage of enabling an operator to vary the dimensions of the surgical opening depending on the requirements of the procedure. Specifically, a plurality of pairs of recesses 519R, 519L may be provided for selectively locating lateral ends 542R, 542L of links 540R, 540L to vary the stroke of a sliding bar 530 in relation to a given movement of elongated portions 510R, 510L. The lateral ends 542R, 542L of the links 540R, 540L may be pivotally attached to the elongated portions 510R, 510L by integral pins 544R, 544L, which may be positioned in recesses 519R, 519L. The integral pins 544R, 544L may be topped by integral caps 545R, 545L which may help retain the pins 544R, 544L within the recesses 519R, 519L.

Positioning the pins 544R, 544L in a pair of recesses 519R, 519L that are closer to a pivot pin 520 may result in the pins 544R, 544L being moved a shorter distance away from one another for a given movement of the elongated portions 510R, 510L. Such a positioning of the pins 544R, 544L may also result in reduction in the angle between the links 540R, 540L. These factors may result in a shorter stroke of the sliding blade 534. Conversely, a longer stroke of the sliding blade 534 may result where the pins 544R, 544L are positioned in a pair of recesses 519R, 519L that are closer to the pivot pin 520. For example, the stroke of the sliding blade 534 may be about 10 mm when the integral pins 544R, 544L are inserted into the recesses 519R, 519L closest to the pivot pin 520 and about 20 mm when the integral pins 544R, 544L are inserted into the recesses 519R, 519L farthest from the pivot pin 520.

In addition, a coil spring 555 may encircle a pin 533 and coil spring ends 556R, 556L may engage the side of the links 540R, 540L closest to the pivot pin 520. The bias of spring 555 may act to keep integral pins 544R, 544L within recesses 519R, 519L as well as bias the handle portions 511R, 511L of elongated portions 510R, 510L apart. The coil spring 555 may also be used in conjunction with one or more leaf springs (discussed above and shown in FIG. 1) to bias handle portions 511R, 511L apart.

The retractor may also comprise support members 590R, 590L as shown in FIGS. 11 and 13. The support members 590R, 590L may be used to support the retractor 500 on a patient's body after the blades 513R, 513L and 534 have been inserted into the patient. Upon insertion, the weight of handle portions 511R, 511L may cause the handle portions 511R, 511L to tip towards the patient, which may cause the blades 513R, 513L and/or 534 to move within a patient. The support members 590R, 590L may by extended and may rest upon the patient's body to oppose any movement created by the weight of handle portions 511R, 511L. And, the support members 590R, 590L may be pivotally mounted on elongated portions 510R, 510L by screws 591R, 591L; however, rivets or other means of providing a pivoting connection may also be used instead of the screws 591R, 591L. Moreover, the support members 590R, 590L may have feet 592R, 592L which may rest on a patient's body when the support members 590R, 590L are pivoted an angle (e.g., 90°) in relation to elongated portions 510R, 510L. As shown in FIG. 13, recessed portions 593L, 594L and similar recess portions on elongate portion 510R (not shown) may be provided within elongated portions 510L, 510R to provide a stowed location (e.g., when 590L is positioned in recess 593L) and a separate deployed location (e.g., when 590L is positioned in recess 594L) for the support members 590L, 590R. These recesses may be oriented either parallel or at an angle (e.g., perpendicular) to elongated portions 510L, 510R and may serve to provisionally lock the support members 590R, 590L in their stowed or deployed positions.

Figure 14:
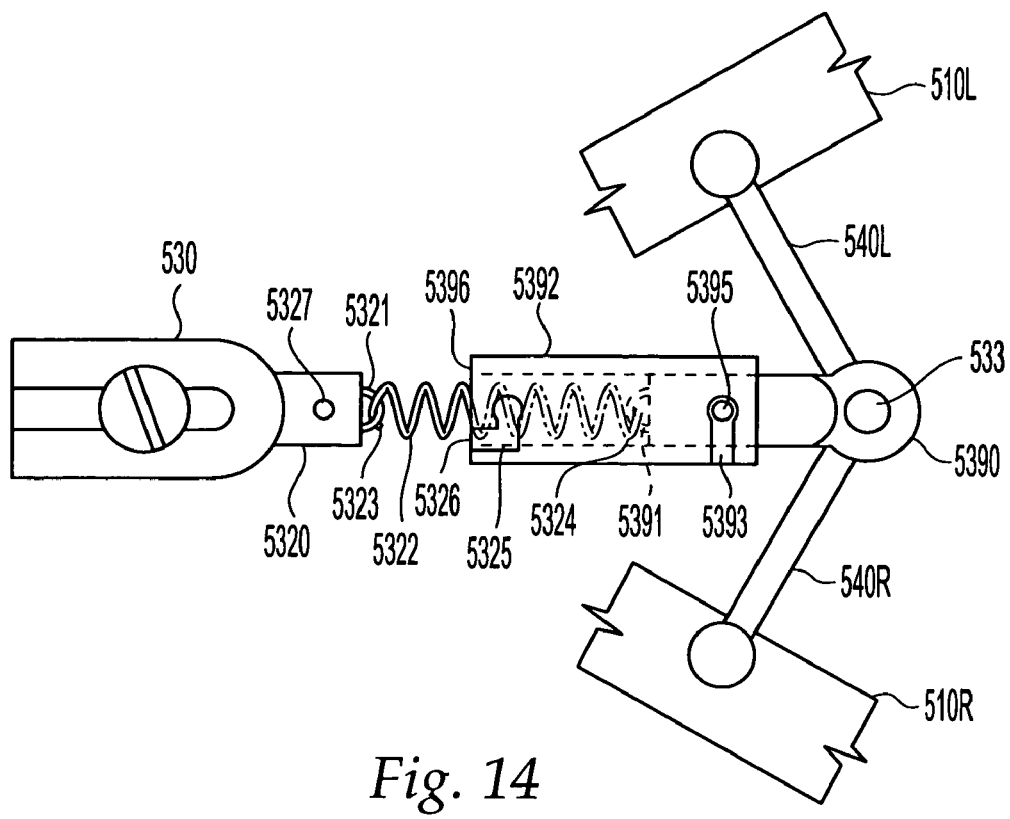
FIG. 14 is a detail of an embodiment of a multiple-blade retractor with a tension limiting device in a first position.
Figure 15:
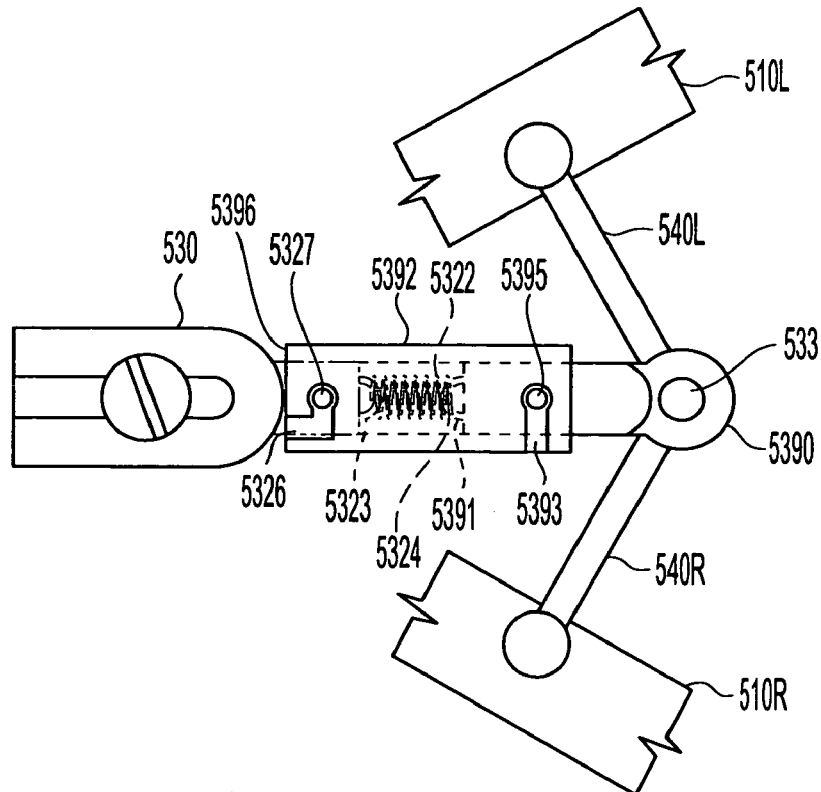
FIG. 15 is a detail of the embodiment of the multiple-blade retractor of FIG. 14 with the tension limiting device in a second position.

The retractor may also comprise a sliding blade tension limiting device, such as shown in FIGS. 14 and 15. In this embodiment, a spring 5322 may be connected to the third blade sliding bar 530 and may limit the amount of force placed on the tissue by the third blade 534 (FIG. 11) during retraction. If the force applied to the tissue being retractor is greater than the spring force, the spring may extend and the third blade 534 may remain stationary or may move only a slight amount, thus reducing the likelihood of tissue damage. For the retractor of this embodiment, the sliding bar 530 may comprise a shortened proximal end 5320 having an attachment means 5321 (e.g., a loop) for attaching to a distal end 5323 of a coil spring 5322. A proximal end 5324 of the spring 5322 may be attached to a connector 5390 by a second attachment means 5391 (e.g., a loop). A pin 533 may pivotally connect the connector 5390 to the links 540R, 540L. So, when the handle portions 511R, 511L are brought together, the third blade 534 may move towards the proximal end of the retractor 500 until the force on the tissue exceeds a predetermined value (corresponding to a selected spring size). At a point after the force on the tissue equals the spring force, the spring may stretch and the blade 534 may remain stationery or may move only slightly. Such a construction may prevent tissue damage. This predetermined maximum tissue force may be controlled by providing the surgeon with a variety of springs to select from, prior to performing the procedure.

In an alternative embodiment, a sleeve 5392 may be provided to allow the sliding blade tension limiting device to be overridden by creating a fixed link between the sliding bar 530 and the connector 5390. The sleeve 5392 may have a proximal circumferential slot 5393 and a distal circumferential slot 5325. A pin 5395 on the connector 5390 may retain the sleeve 5392 on the connector 5390 by engaging a slot 5393, while still allowing the sleeve 5392 to be rotated about the connector 5390. A longitudinal slot 5326 may allow a distal end 5396 of the sleeve 5392 to be slid over a pin 5327 on the proximal end 5320. The sleeve 5392 may then be rotated so that it may be retained on the proximal end 5320 of the sliding bar 530. In this configuration, shown in FIG. 15, the sliding bar 530 and the connector 5390 may be held in a fixed relationship so that the retractor may operate similar to the retractor 100 of FIGS. 1-3. While a sleeve is shown as a means of removably providing a nonelastic bridge over the gap between the sliding bar 530 and the connector 5390, other means are also envisioned including, for example, a screw which may be removeably or permanently fixed to the connector 5390 and may be screwed into a portion the sliding bar 530 (i.e., engaged or disengaged) or vice versa such as discussed below.

Figure 16:
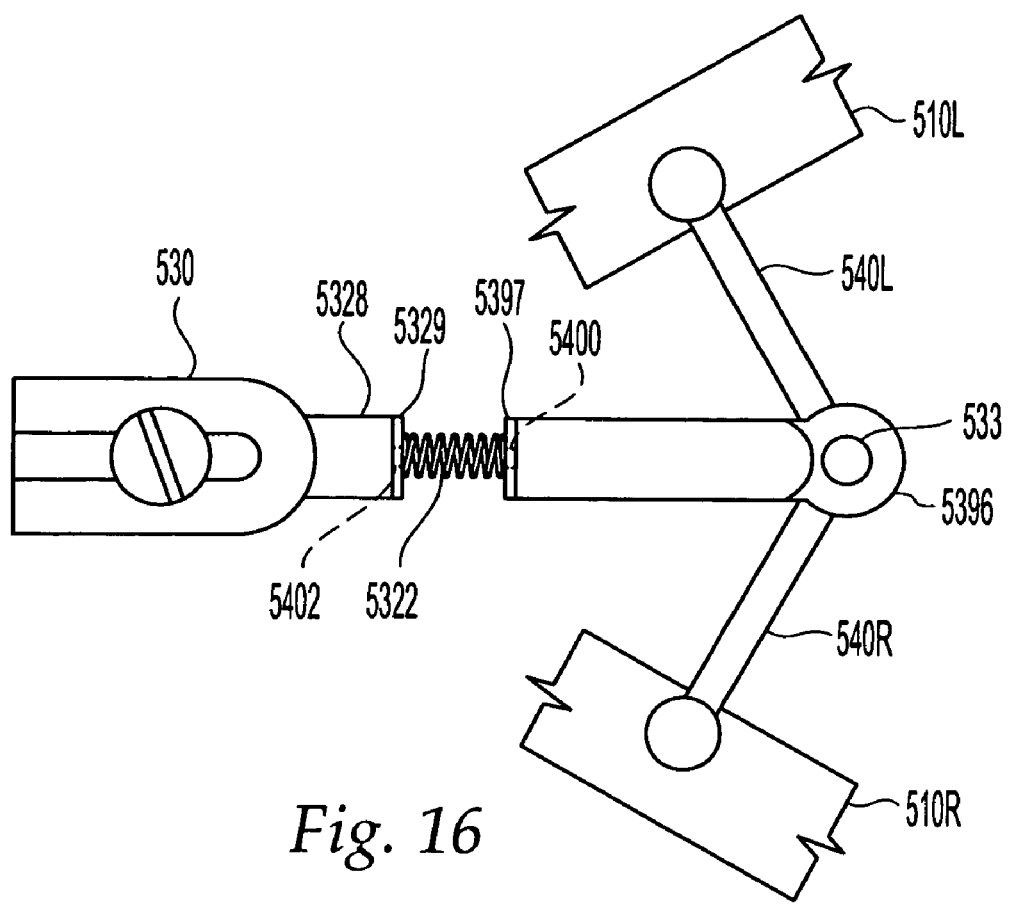
FIG. 16 is a detail of an embodiment of a multiple-blade retractor with an alternative tension limiting device in a first position.
Figure 17:
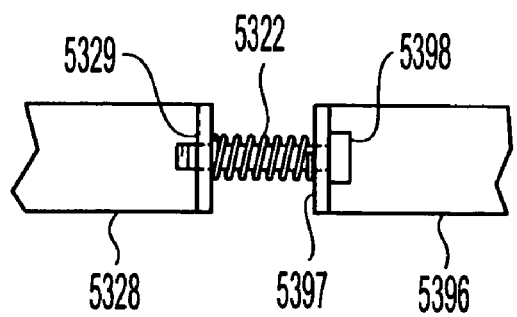
FIG. 17 is a detail of an embodiment of the multiple-blade retractor of FIG. 16 with the alternative tension limiting device in a second position.

FIGS. 16 and 17 illustrate an alternative means for limiting the force applied to an incision by the sliding blade 530. A horizontal member 5328 may be attached to the proximal end of the sliding bar 530 and may have at its proximal end a threaded receiving member 5329. The member 5396 may extend from the pin 533 to a vertical member 5397. A spring 5322 may connect the vertical member 5397 and the threaded receiving member 5329 to limit the force applied to an incision by the third blade 534 in the same manner as the sliding blade tension limiting device shown in FIG. 14.

The force limiting device of FIGS. 16 and 17 may be overridden. The vertical member 5397 may have a through hole 5400 and the receiving member 5329 may have a threaded hole 5402. A connecting component 5398 (e.g., a screw) may be inserted through the hole of the vertical member 5397 and threaded into the threaded hole of the receiving member 5329. Thus, the member 5396 may be fixed with respect to the sliding bar 530. It should be noted that other methods and mechanisms may be used to limit the force applied to an incision by the sliding blade 534. Likewise, other arrangements may be used to override such tension limiting mechanisms.

FIGS. 18 and 19 show an embodiment of a retractor 600 with a detachable and independently moveable fourth blade 690 which may be located opposite a sliding blade 634. While shown as detachable, fourth blade 690 may also be permanently attached. The detachable fourth blade 690 may allow a surgeon to further vary the shape and dimensions of the opening created by the retractor 600. The fourth blade 690 may be attached to slotted arms 691R, 691L by pivot pins 692R, 692L. However, other means of attaching the fourth blade 690 to the retractor 600 are also envisioned. In addition, the fourth blade 690 may have all the features of the previously described blades. For example, the fourth blade 690 may have a flared end, may be adjustable similar to the blade 313 (FIGS. 6-8) or may have a cannula similar to cannula 1341 (FIG. 9). Screws 693R, 693L, which extend through slots 694R, 694L of the arms 691R, 691L, may be used to attach the arms 691R, 691L to the elongated portions 610R, 610L. The screws 693R, 693L may be threaded into thread holes (not shown) in the elongated portions 610R, 610L. Other components such as bolts may be used in place of the screws 693R, 693L. It will be apparent to those skilled in the art that any method of connecting the fourth blade 690 to the retractor 600 is envisioned.

In use, a surgeon may loosely attach the arms 691R, 691L to the elongated portions 610R, 610L using screws 693R, 693L. Thereafter, the surgeon may open and lock the retractor 600 within the patient and may manually move the fourth blade 690 into a desired position. The fourth blade 690 may be held in the desired position while the screws 693R, 693L are rotated until the arms 691R, 691L are locked in position. Thus, a four-pointed square or roughly circular opening may be formed. The dimension from the blade 613R to the blade 613L, for example, may be between about 10 mm and about 150 mm. And, the dimension from the sliding blade 634 to the fourth blade 690 may be between about 10 mm and about 70 mm.

FIG. 20 shows an alternative means of connecting the fourth blade 690 to the retractor 600. Rather than having pivot points at each end, the blade 690 may have a single pivot 692 at its center and a unitary arm 691 which may have slots 694R, 694L. The arrangement shown in FIGS. 20 may be used in the same way as described above with regard to FIGS. 18 and 19.

But, unlike the arrangement show in FIGS. 18 and 19, the fourth blade 690 of FIG. 20 may be allowed to pivot after arm 691 is locked. Alternatively, the pivot 692 may be fixed so that the fourth blade 690 is held in place.

Figure 21:
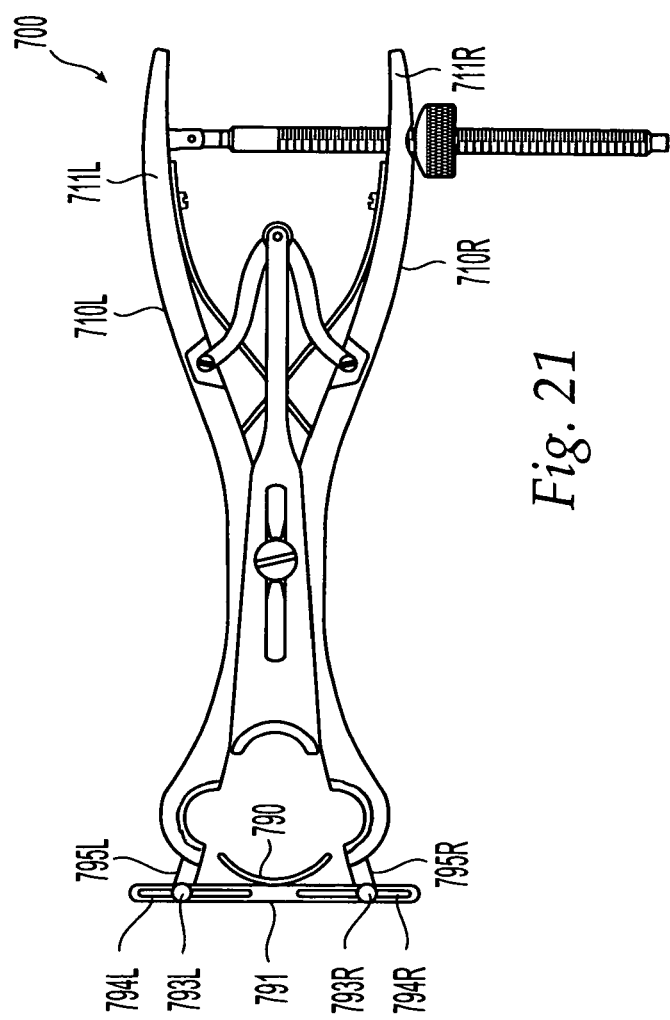
FIG. 21 is a bottom view of another alternative embodiment of a multiple-blade retractor with an alternative fourth blade attachment.
Figure 22:
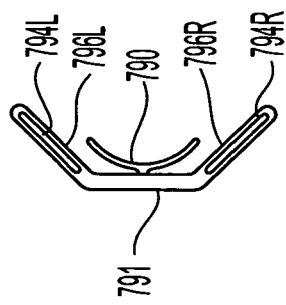
FIG. 22 is a top view of an alternative fourth blade attachment of the multiple-blade retractor of FIG. 21.

FIGS. 21 and 22 show another embodiment of a retractor 700 comprising a fourth blade 790, which may be permanently attached to or detachable from the retractor 700. The fourth blade 790 may be connected to the arm 791 by, for example, welding, brazing, or mechanical connectors such as rivets or screws (not shown). The arm 791, in turn, may be attached to tabs 795R, 795L on elongated portions 710R, 710L by connectors 793R, 793L. The connectors 793R, 793L may slide within the slots 794R, 794L in arm 791. Various components may be used as connectors 793R, 793L, including a pin, screw, or bolt.

In use, a surgeon may loosely attach the arms 791 to the elongated portions 710R, 710L using connectors 793R, 793L. After opening and locking the retractor 700, the surgeon may manually move the fourth blade 790 into position (e.g, by moving the arm 791 back and forth so that the connectors 793R, 793L move within the slots 794R, 794L) and hold the blade 790 in position while tightening the connectors 793R, 793L. After the connectors 793R, 793L are fully tightened, the fourth blade 790 may be locked in position. The fourth blade 790 may have all the features of previously described blades including, for example, a flared end, adjustability (e.g., similar to the blade 313 of FIGS. 6-8), and may also have a cannula for holding various instruments (FIG. 9).

As shown in FIG. 22, the arm 791 may have angled portions 796R, 796L rather than the straight arm 791 of FIG. 21. The angled portions 796R, 796L may allow the fourth blade 790 to move in a distal direction as the handle portions 711R, 711L are brought together or a proximal direction as the elongate portions 710R, 710L move apart from each other. The angled portions 796R, 796L may be various lengths and form various angles in relation to each other to allow for a wide range of movement.

Figure 23:
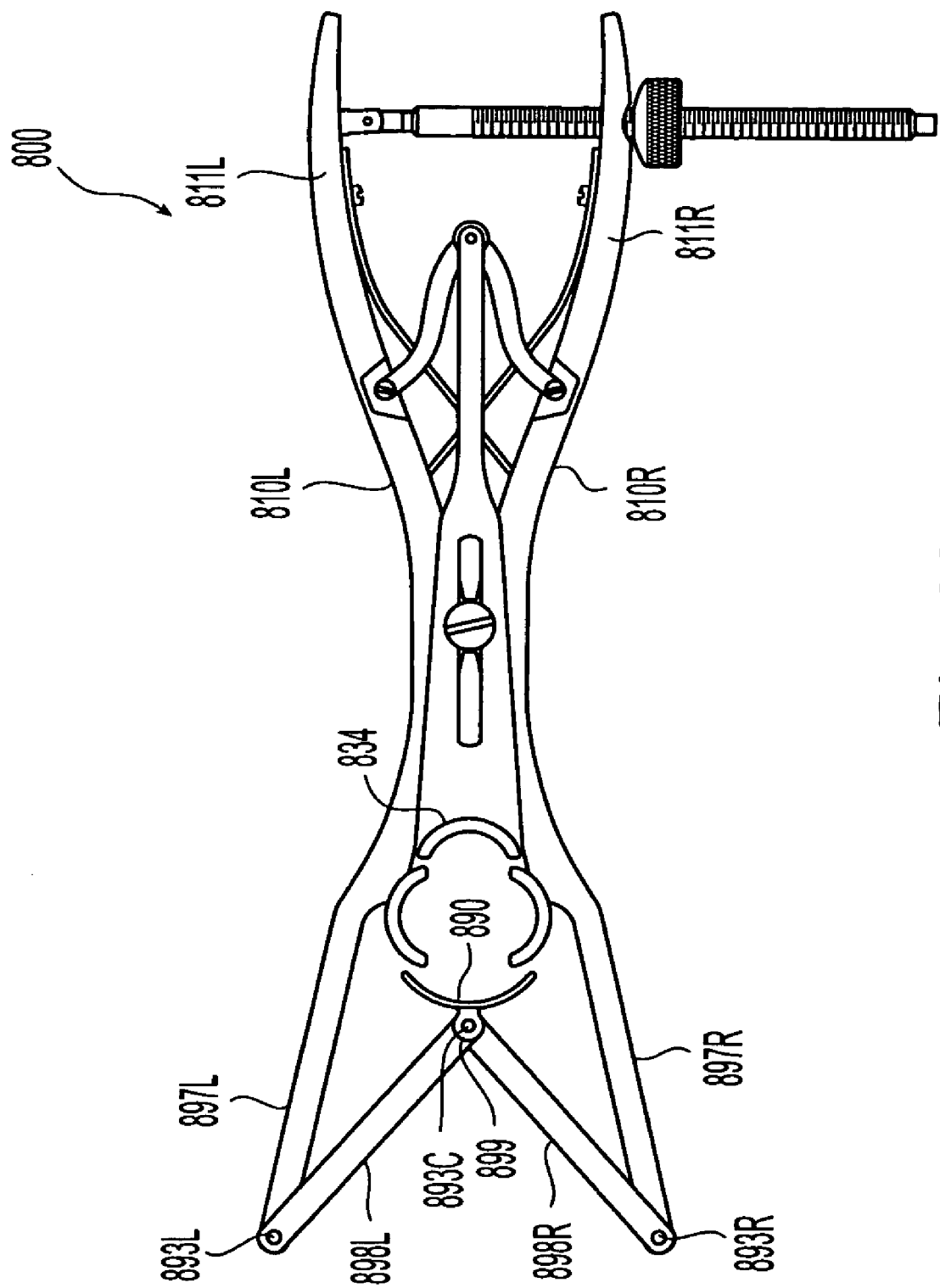
FIG. 23 is a bottom view of another alternative embodiment of a multiple-blade retractor with another alternative fourth blade attachment.

FIG. 23 shows an embodiment of a retractor 800 with a fourth blade 890, which may move as the other blades are moved. Elongated portions 810R, 810L may have extension arms 897R, 897L, which may be integral with the elongated portions 810R, 810L or with may be removeably attached to the elongated portions 810R, 810L by screws or other appropriate mechanical means. The extension arms 897R, 897L may be connected to arms 898R, 898L, which may pivot about pins 893R, 893L. Additionally, the arms 898R, 898L may be pivotally attached to a member 899 at a central pin 893C. And, the blade 890 may be attached to member 899 by, for example, welding, brazing, or a mechanical connection (e.g., a rivet, screw, bolt, etc.). In use, handle portions 8111R, 8111L of elongated portions 810R, 810L may be brought together and the pins 893R, 893L may move farther apart. As a result, the arms 898R, 898L may pivot about the pins 893R, 893L, thereby moving the member 899 along with the fourth blade 890 away from a sliding blade 834. The movement of the fourth blade 890 may make the retractor 800 easier to use than the retractors of FIGS. 18-22 (i.e., does not require the surgeon to perform the addition step of adjusting the fourth blade). The retractor 800 may, however, be less flexible in use since the blades are in a set relationship with respect to each other. The fourth blade 890 may have all the features of previously described blades including, for example, a flared end, adjustability (e.g., similar to the blade 313 of FIGS. 6-8), and may also have a cannula for holding various instruments (FIG. 9).

Figure 24:
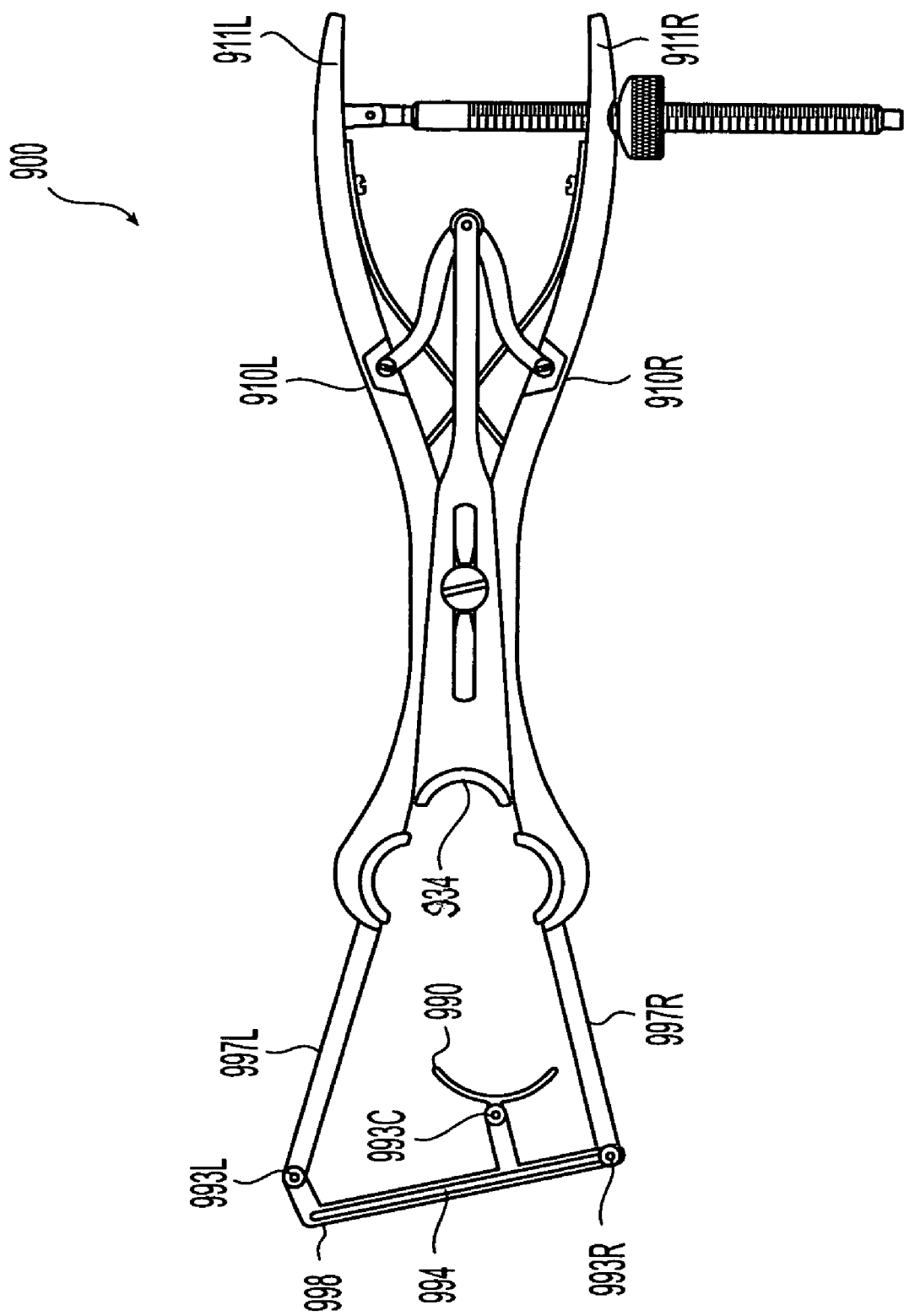
FIG. 24 is a bottom view of another alternative embodiment of a multiple-blade retractor with another alternative fourth blade attachment.

FIG. 24 illustrates another retractor 900 where a fourth blade 990 may move as the other blades move. The elongated portions 910R, 910L may have extension arms 997R, 997L. As handle portion 9111R, 911L are brought together, an arm 998 may pivot about a pin 993L at the distal end of the extension arm 997L and a pin 993R may slide within a slot 994 of the arm 998. The movement of the arm 998 may result in the fourth blade 990, which may be attached to the arm 998 by a pin 993C, moving in a distal direction, away from a sliding blade 934. The fourth blade 990 may pivot about the pin 993C or may be fixed with respect to the arm 998.

Furthermore, the retractors described herein may be provided as an individual component, or it may be provided as part of a kit. A kit may include one or more of the retractors described herein, and one or more two-bladed retractors or two-bladed hinged retractors. The two-bladed and two-bladed hinged retractors may be obtained from any number of fabricators of medical instruments. As part of a kit, the retractor may be provided with a multiplicity of interchangeable blades comprising various lengths, materials, and surface configurations, as well as various springs for the force-limiting sliding blade embodiments. A kit may also contain a light source, suction/irrigation tool, flat blades, blades of various lengths, and blades of various engagement angles.

While the foregoing description and drawings represent the preferred embodiments of the present invention, it will be understood that various additions, modifications and substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. The presently disclosed embodiments are therefore to be considered in all respects as illustrative and not restrictive, the scope of the invention being indicated by the appended claims, and not limited to the foregoing description.

What is claimed is:

1. A surgical retractor for inserting into an opening in a patient comprising:
   a first elongated member having a proximal end, a distal end and a projection, a second elongated member having a proximal end, a distal end, a recess and a projection, the projection of the first elongated member being positioned in the recess of the second elongated member when the second elongated member is connected to the first elongated member via a pivot pin, the pivot pin passing through the projections of the first and second elongated members;
   a third elongated member having a proximal end and a distal end, wherein the third elongated member is connected to the first and second elongated members at the pivot pin connecting the first and second elongated members and wherein the third elongated member is also connected to the first elongated member via a first link and to the second elongated member via a second link;
   a first blade having a first end and a second end, the first end of the first blade being directly connected to the distal end of the first elongated member, the second end of the first blade being configured to be insertable into the opening in the patient;

a second blade having a first end and a second end, the first end of the second blade operatively associated with the distal end of the second elongated member, the second end of the second blade being configured to be insertable into the opening in the patient; and a third blade having a first end and a second end, the first end of the third blade operatively associated with the distal end of the third elongated member, the second end of the third blade being configured to be insertable into the opening in the patient; wherein:

the first and second elongated members engage each other so that movement of the proximal ends of the first and second elongated members towards each other causes the distal ends of the first and second elongated members to move away from each other.

2. The surgical retractor of claim 1, wherein the third elongated member comprises a slidable member associated with the first end of the third blade, the slidable member being connected to the first and second elongated members such that movement of the first and second blades relative to each other results in movement of the slidable member relative to the first and second elongated members.

3. The surgical retractor of claim 1, wherein at least one of the first, second, and third blades has a length in the range of about 25 mm to about 200 mm.

4. The surgical retractor of claim 3, wherein the length of at least one blade is adjustable.

5. The surgical retractor of claim 1, wherein the first and second blades have a first length and the third blade has a second length, the second length being less than the first length.

6. The surgical retractor of claim 1, wherein the first and second blades have a first length and the third blade has a second length, the second length being greater than the first length.

7. The surgical retractor of claim 1, wherein at least one of the first and second elongated members comprises a grip portion.

8. The surgical retractor of claim 1, wherein the distal tip of at least one of the first, second, and third blades has an angle of about 90° to about 180°.

9. The surgical retractor of claim 1, wherein the distal tip portion of at least one of the first, second, and third blades has a radius between about 0 mm and about 100 mm.

10. The surgical retractor of claim 1, wherein at least one of the first, second, and third blades is made of radiolucent material.

11. The surgical retractor of claim 1, wherein at least one of the first, second, and third blades is removable.

12. The surgical retractor of claim 11, wherein the at least one removable blade is attached by a ball-detent mechanism.

13. The surgical retractor of claim 11, wherein the at least one removable blade is attached by a screw.

14. The surgical retractor of claim 1, wherein at least one of the first, second, and third blades has a cannula.

15. The surgical retractor of claim 1, wherein at least one of the first, second, and third blades has an integral light source.

16. The surgical retractor of claim 1, wherein at least one blade has an attachment mechanism for at least one of the group consisting of a light source, a suction device, a microscope, and an endoscope.

17. The surgical retractor of claim 1, wherein at least one of the first, second, and third blades has an integral irrigation source.

18. The surgical retractor of claim 1 further comprising a connecting portion for fixing the retractor in place during surgery.

19. The surgical retractor of claim 1, wherein moving the proximal ends of the first and second elongated members closer to each other results in the third blade moving away from the first and second blades by an amount proportional to the movement of the first and second elongated members.

20. The surgical retractor of claim 1, wherein the first link is adjustable relative to the first elongated member and the second link is adjustable relative to the second elongated member, the adjustable first and second links affecting the movement of the third blade relative to the first and second blades.

21. The surgical retractor of claim 1, wherein the first and second links are adjustable to allow adjustment of the proportion of third blade movement produced by the movement of the first and second elongated members.

22. The surgical retractor of claim 1, further comprising a support member for at least one of the first and second elongated members.

23. The surgical retractor of claim 1, wherein the opening produced is approximately triangular having a first dimension of between about 10 mm and about 150 mm, and a second dimension of between about 10 mm and about 50 mm.

24. The surgical retractor of claim 1, wherein the opening produced is polygonal having a first dimension of between about 10 mm and about 150 mm, and a second dimension of between about 10 mm and about 70 mm.

25. The surgical retractor of claim 1, wherein the length of at least one of the blades is adjustable.

26. The surgical retractor of claim 1, the second end of the first, second and third blades are flared.

* * * * *